US010166390B2

(12) United States Patent
Fueglister

(10) Patent No.: US 10,166,390 B2
(45) Date of Patent: Jan. 1, 2019

(54) HELICAL INSERTER

(76) Inventor: Fabian Hermann Urban Fueglister, Würenlos (CH)

(*) Notice: Subject to any disclaimer, the term of this patent is extended or adjusted under 35 U.S.C. 154(b) by 1155 days.

(21) Appl. No.: 13/990,434

(22) PCT Filed: Nov. 30, 2011

(86) PCT No.: PCT/IB2011/002878
§ 371 (c)(1),
(2), (4) Date: May 30, 2013

(87) PCT Pub. No.: WO2012/073097
PCT Pub. Date: Jun. 7, 2012

(65) Prior Publication Data
US 2013/0253532 A1 Sep. 26, 2013

Related U.S. Application Data

(60) Provisional application No. 61/417,937, filed on Nov. 30, 2010.

(51) Int. Cl.
*A61B 17/062* (2006.01)
*A61N 1/36* (2006.01)
*A61B 17/06* (2006.01)
*A61B 17/34* (2006.01)
*A61N 1/05* (2006.01)

(52) U.S. Cl.
CPC ........ *A61N 1/36078* (2013.01); *A61B 17/062* (2013.01); *A61B 17/06066* (2013.01);
(Continued)

(58) Field of Classification Search
CPC ........ A61B 17/062; A61B 2017/06076; A61B 2017/06052; A61B 2017/06171;
(Continued)

(56) References Cited

U.S. PATENT DOCUMENTS 3,035,580 A * 5/1962 Methodi Guiorguiev ................... A61B 18/14
604/20
5,356,424 A * 10/1994 Buzerak ............ A61B 17/0469
112/169

(Continued)

OTHER PUBLICATIONS

Tetsuo Inoue, Notice of Rejection for associated application JP2013-541437, dated Oct. 26, 2015, Japanese Patent Office, Japan.

*Primary Examiner* — Diane Yabut
(74) *Attorney, Agent, or Firm* — Babcock IP, PLLC

(57) ABSTRACT

A method and apparatus for inserting inserts helically into soft tissue is provided. The inserter is made up of a housing assembly, a hollow helical needle; and a matched first and second hypoid gear. In its basic form, the apparatus includes a housing assembly, a hollow helical insert guide, a helical insert drive and a guide removal device. The hollow helical insert guide is held in functional relationship by the housing assembly and is adapted to be loaded with the insert for helical transport therewith into the soft tissue. The helical insert drive drives the helical insert guide in rotation and translation into the soft tissue. When an insert is present within the insert guide, the guide removal device removes the insert guide while leaving the insert in its intended implant location in the soft tissue. The method and apparatus insert an implantable member helically into soft tissue, thereby better fixing the implantable member in the soft tissue when such tissue is deformed.

35 Claims, 32 Drawing Sheets

(52) U.S. Cl.
CPC ........ *A61B 17/3468* (2013.01); *A61N 1/0526* (2013.01); *A61B 2017/06052* (2013.01); *A61B 2017/06076* (2013.01); *A61N 1/0573* (2013.01); *A61N 1/3601* (2013.01); *A61N 2001/0578* (2013.01)

(58) Field of Classification Search
CPC .............. A61N 1/36078; A61N 1/0573; A61N 1/0575; A61N 2001/0578; A61F 5/56
See application file for complete search history.

(56) References Cited

U.S. PATENT DOCUMENTS

| | | | | |
|---|---|---|---|---|
| 5,782,844 | A * | 7/1998 | Yoon | A61B 17/064 606/139 |
| 6,016,809 | A * | 1/2000 | Mulier | A61B 18/1477 128/898 |
| 7,328,071 | B1 * | 2/2008 | Stehr | A61N 1/0587 600/585 |
| 7,458,940 | B2 * | 12/2008 | Miller | A61B 10/0096 600/564 |
| 7,461,767 | B2 * | 12/2008 | Viola | A61B 17/07207 227/175.2 |
| 2008/0103407 | A1 * | 5/2008 | Bolea | A61N 1/0556 600/529 |
| 2009/0216108 | A1 * | 8/2009 | Barrera | A61B 5/02007 600/410 |
| 2010/0137878 | A1 * | 6/2010 | Truong | A61N 1/0573 606/129 |

* cited by examiner

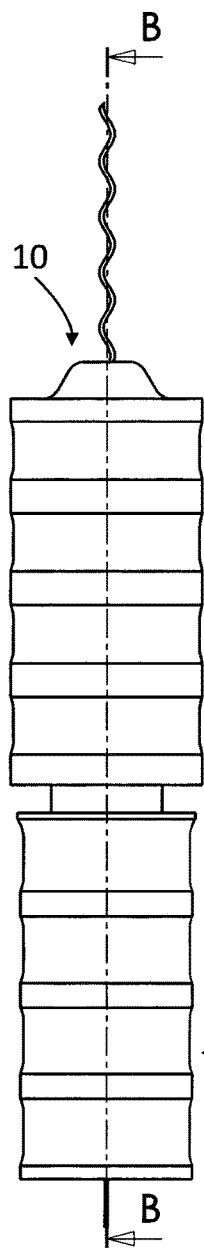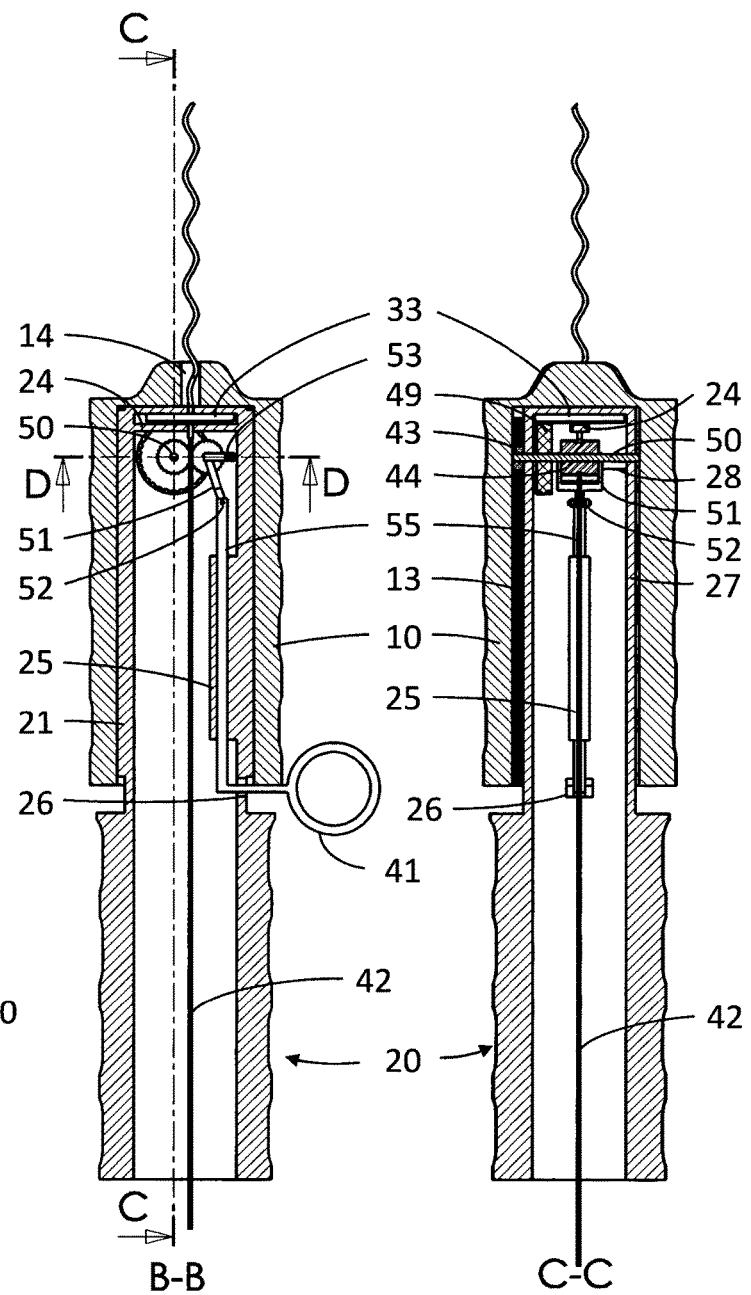
FIG. 3A    FIG. 3B    FIG. 3C

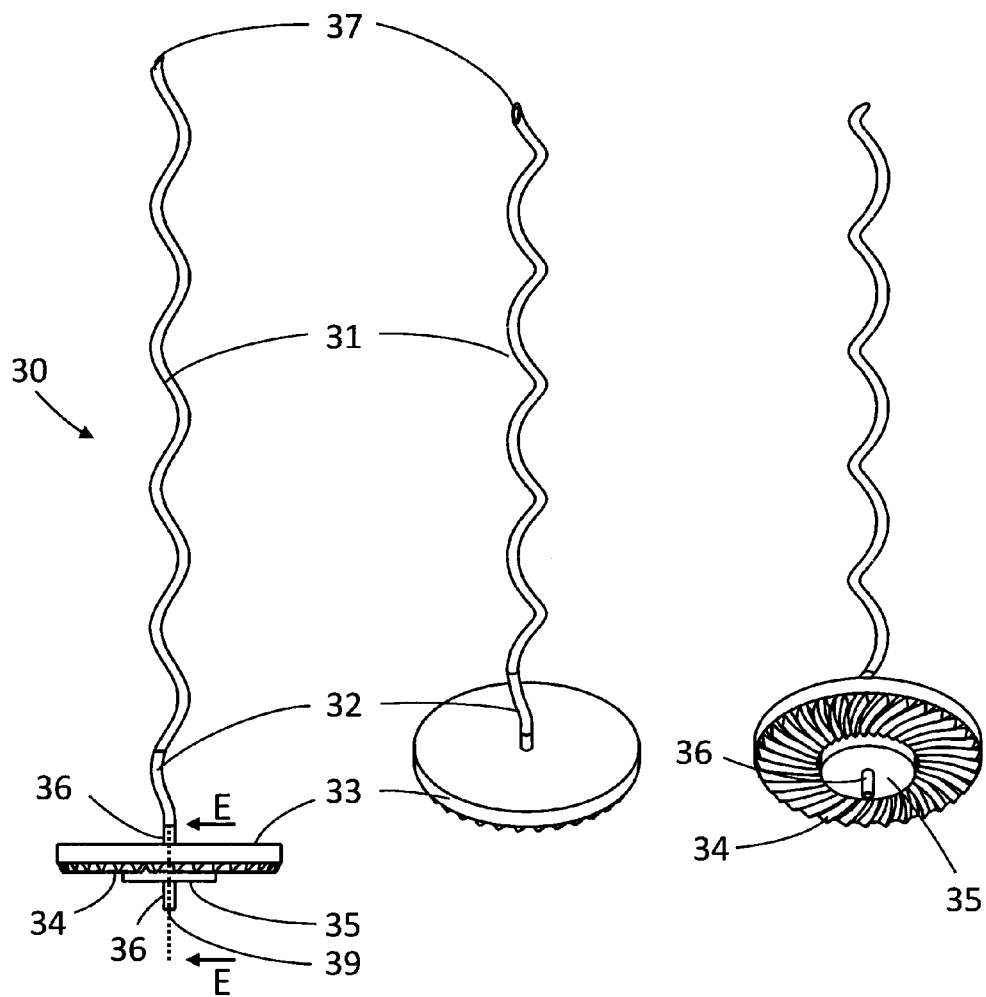
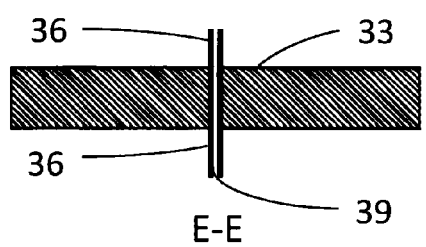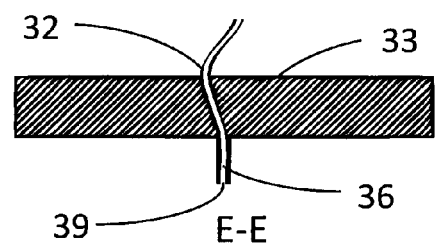
FIG. 6A    FIG. 6B

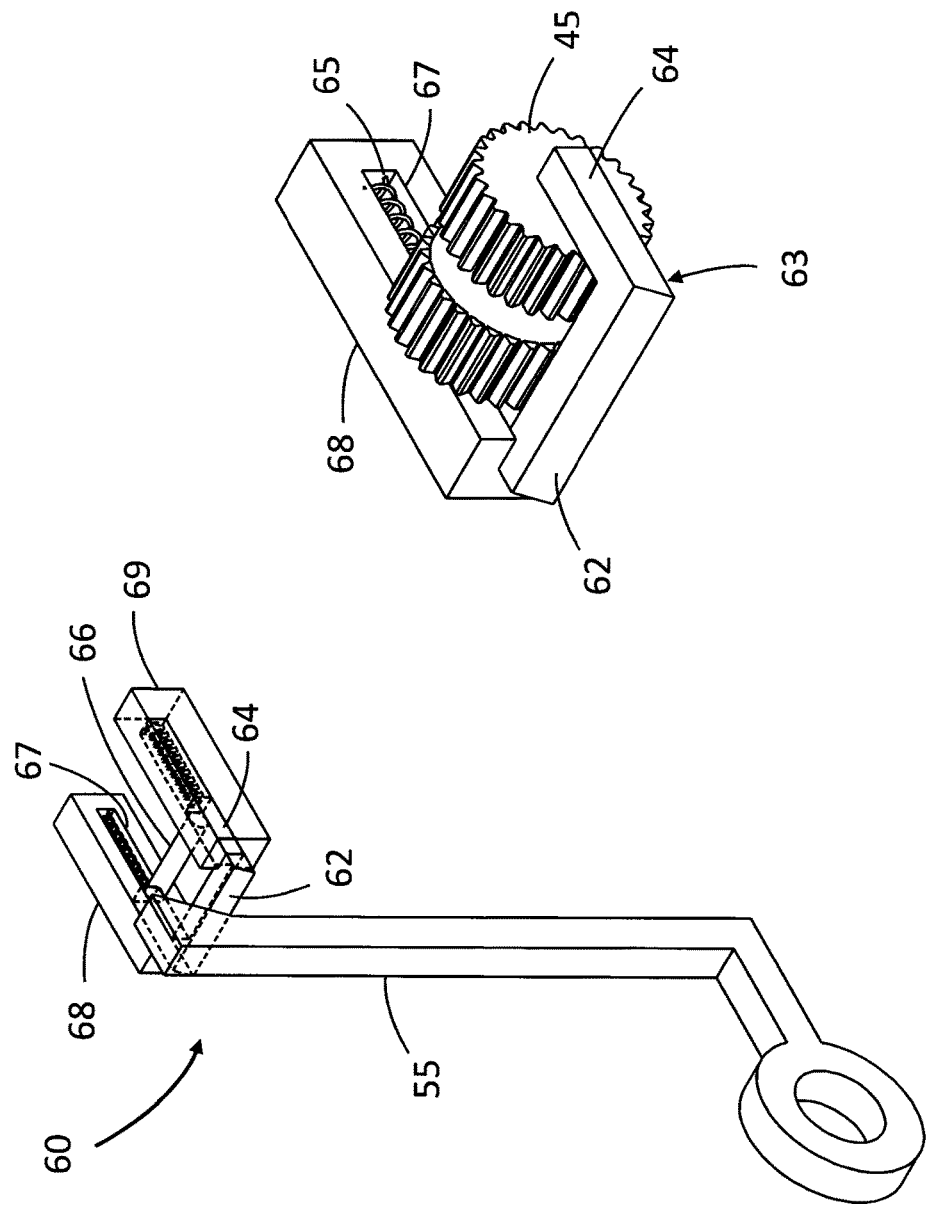

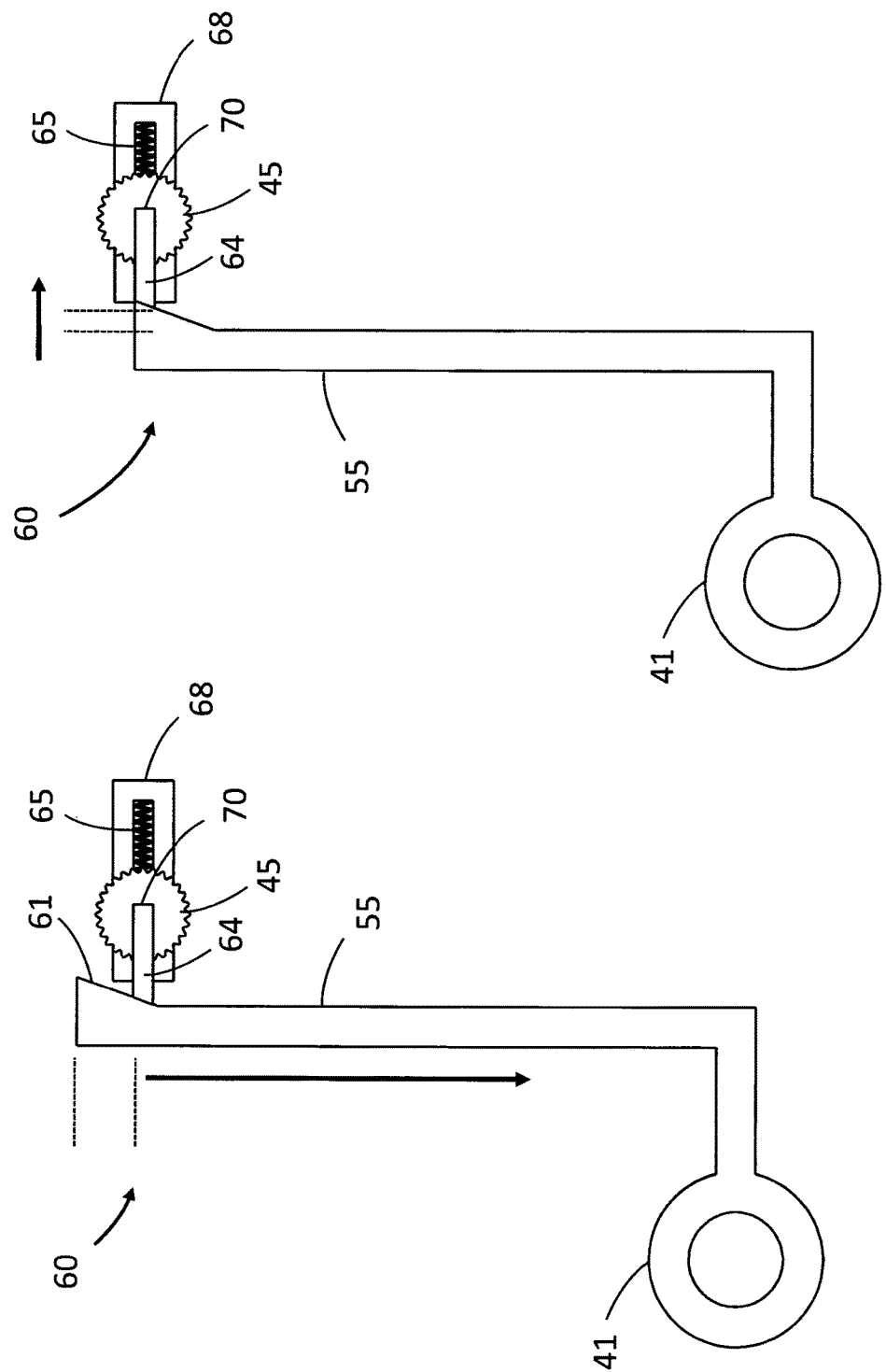

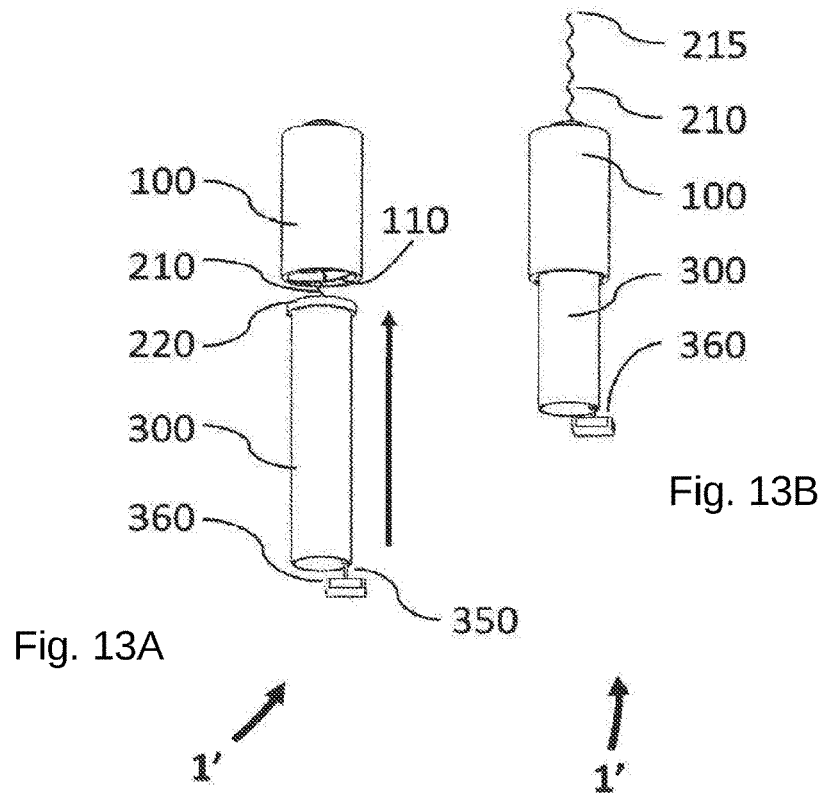
Fig. 13A
Fig. 13B
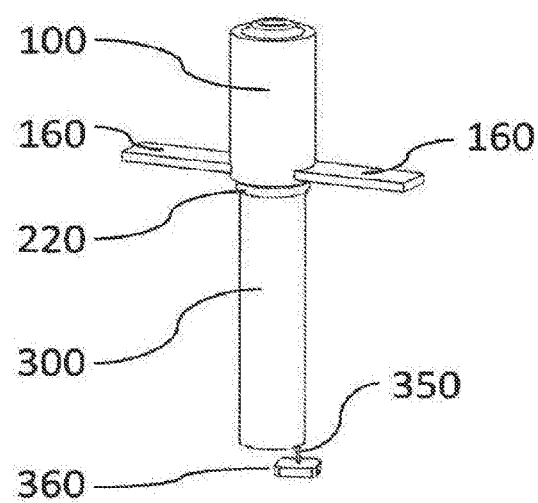
Fig. 14

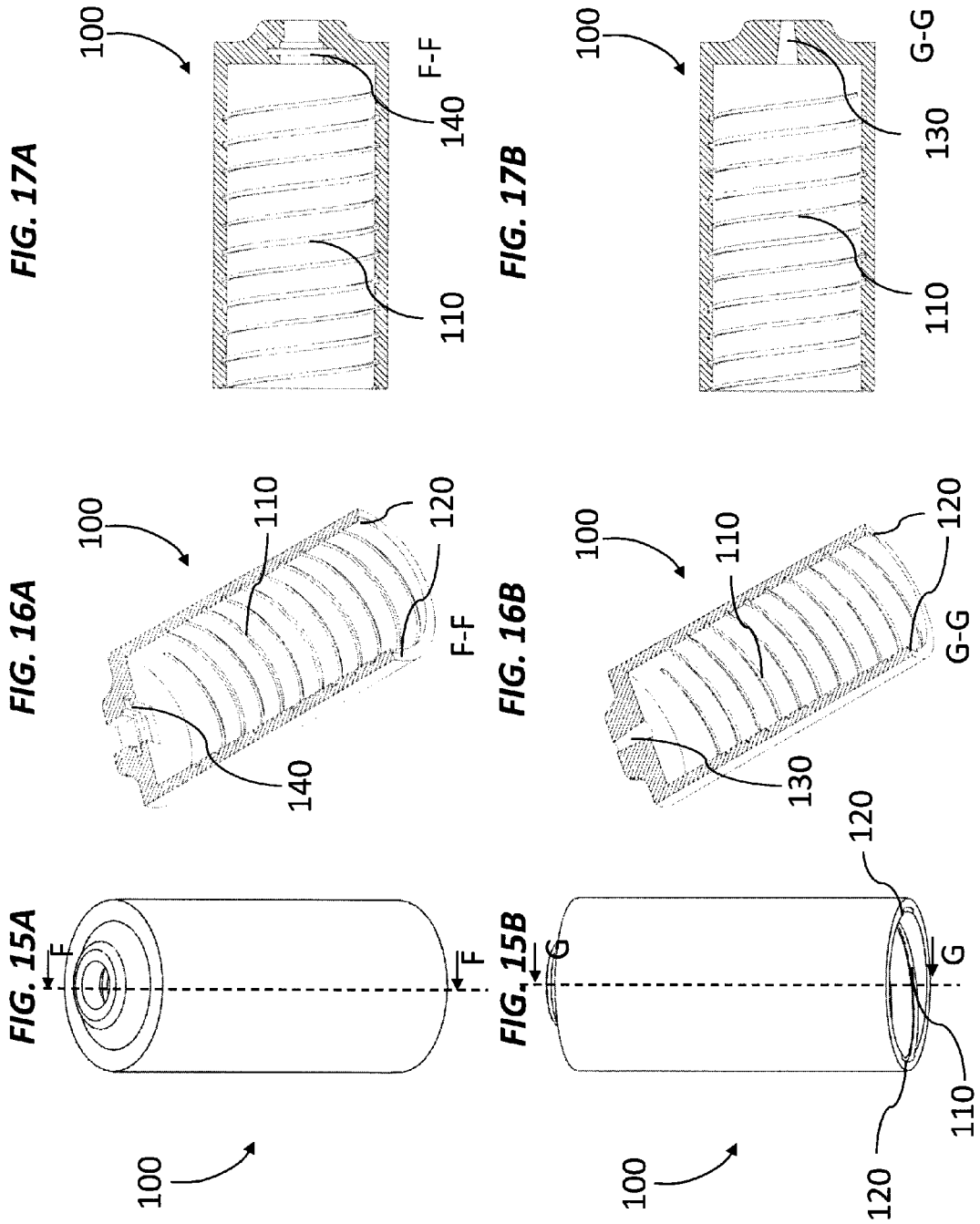

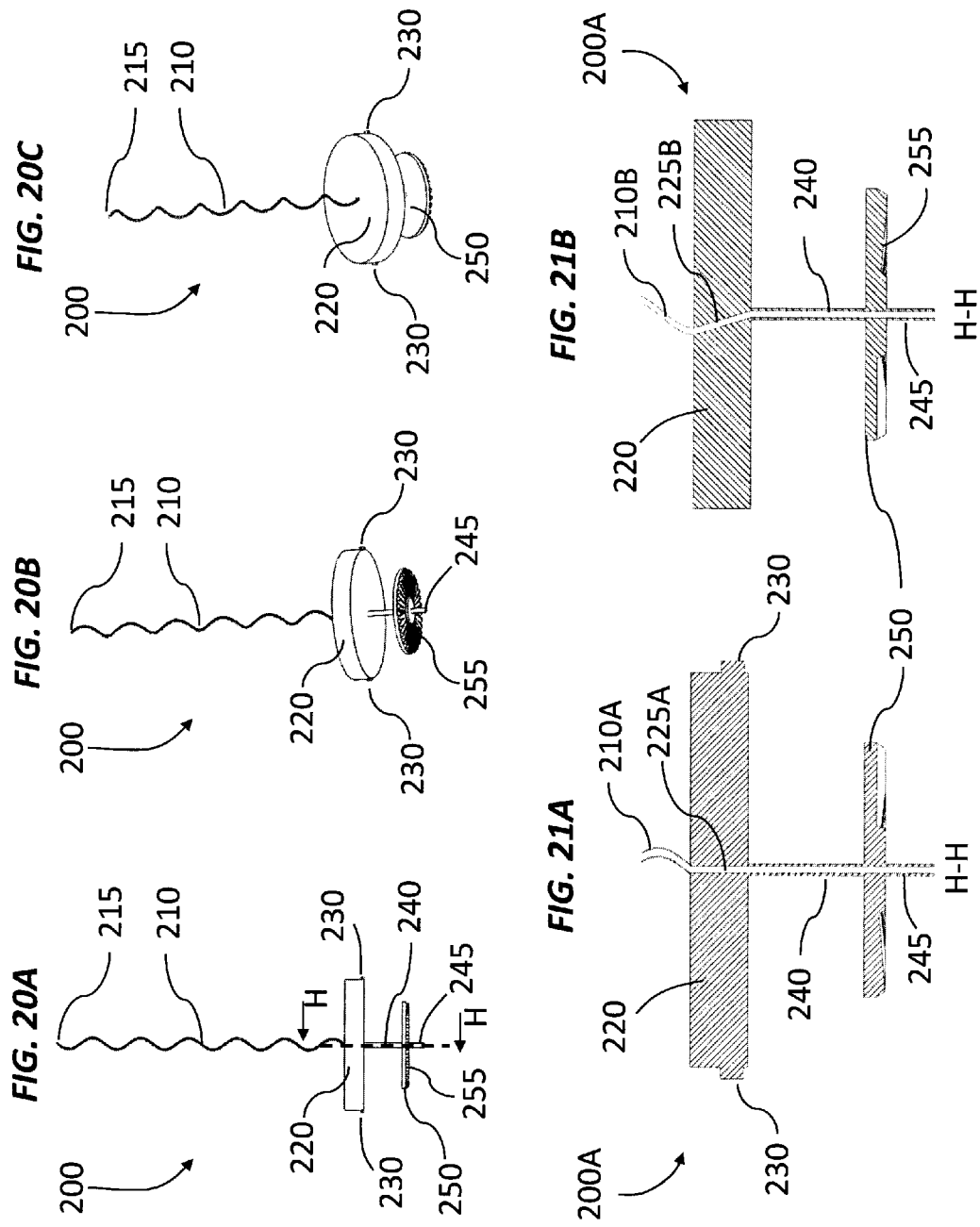

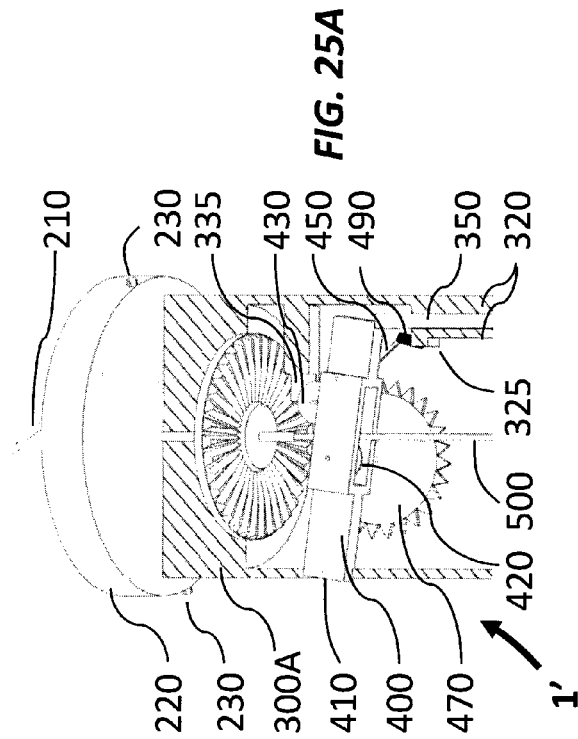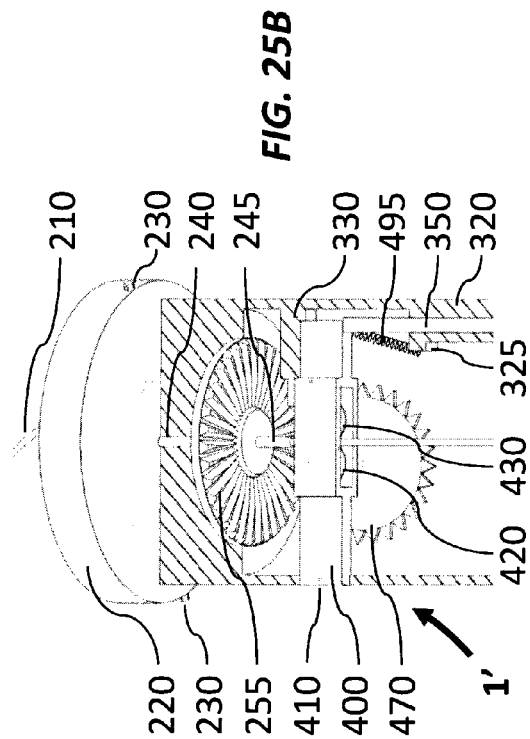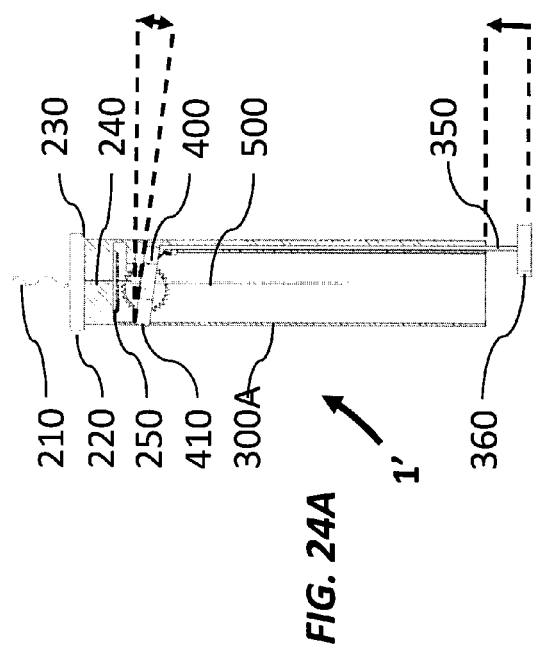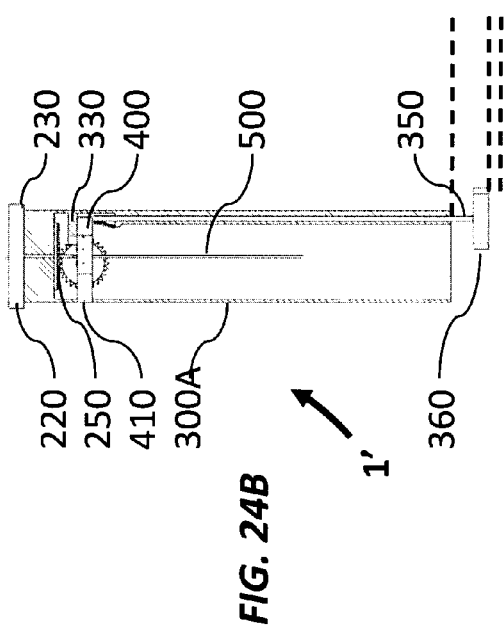
FIG. 24A
FIG. 24B
FIG. 25A
FIG. 25B

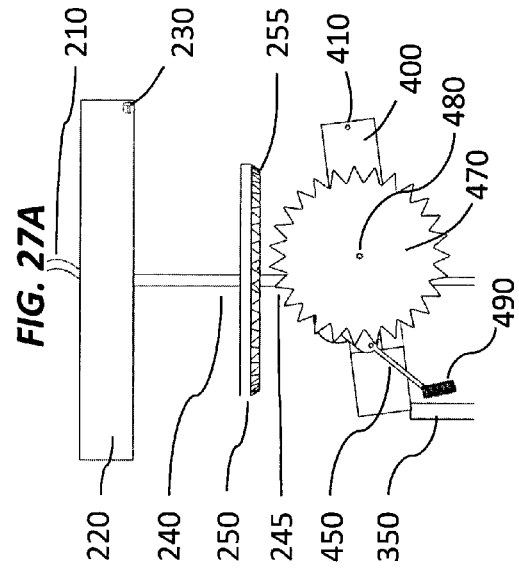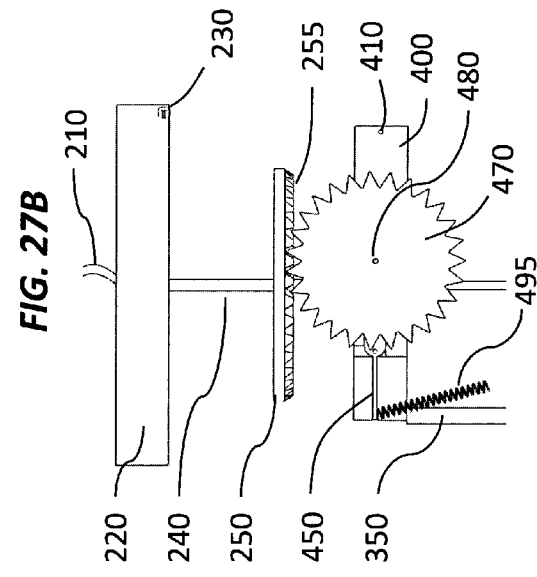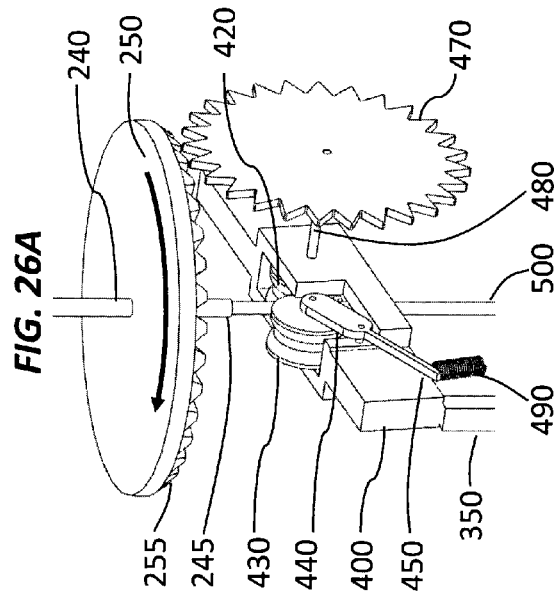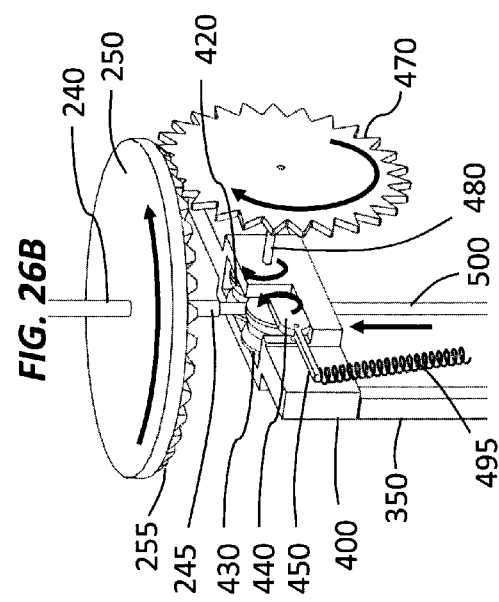

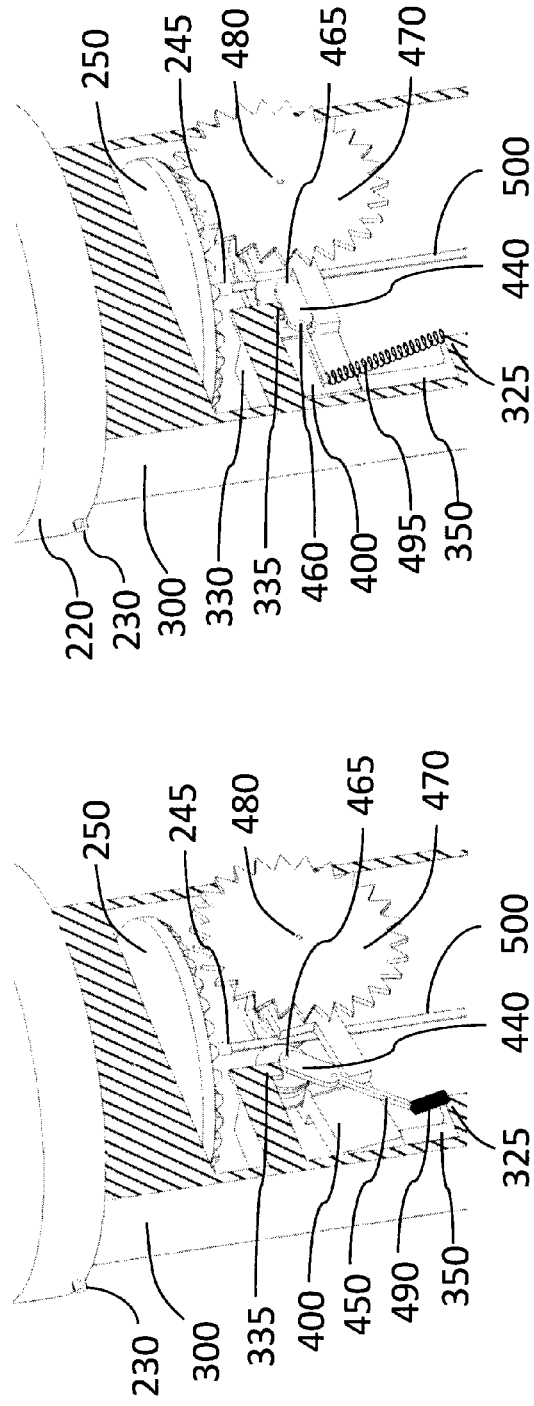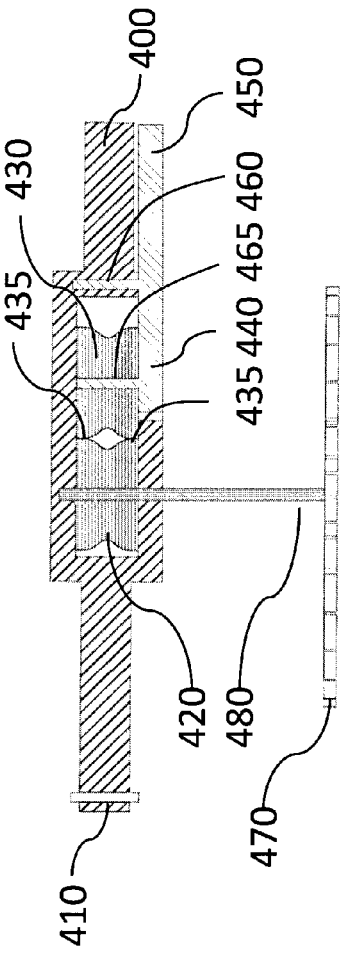

Alt. D-D

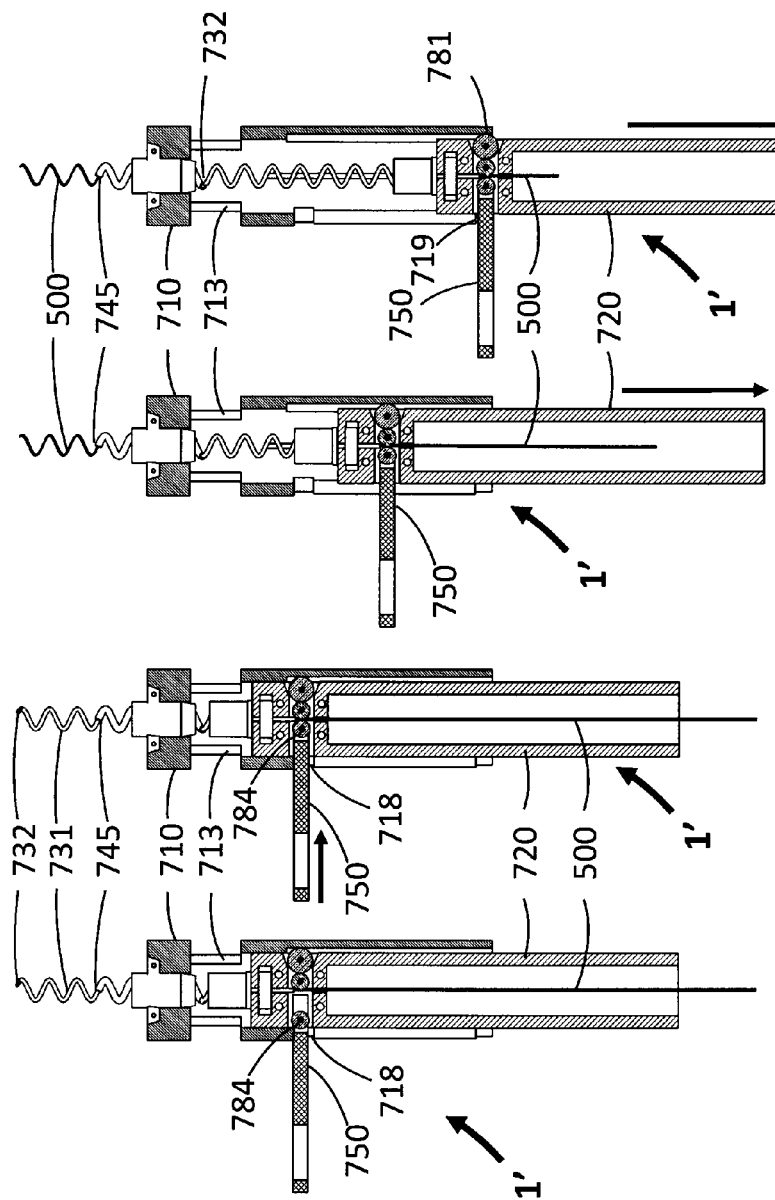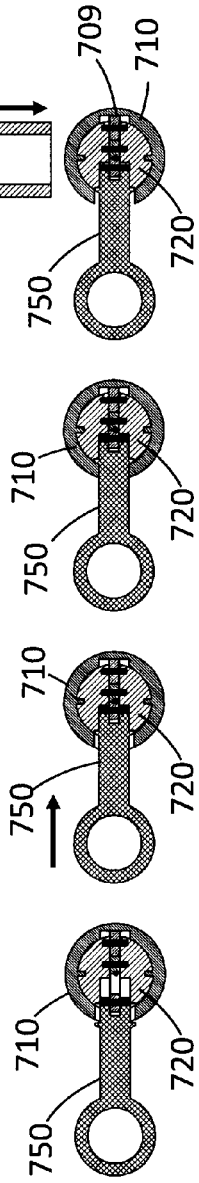

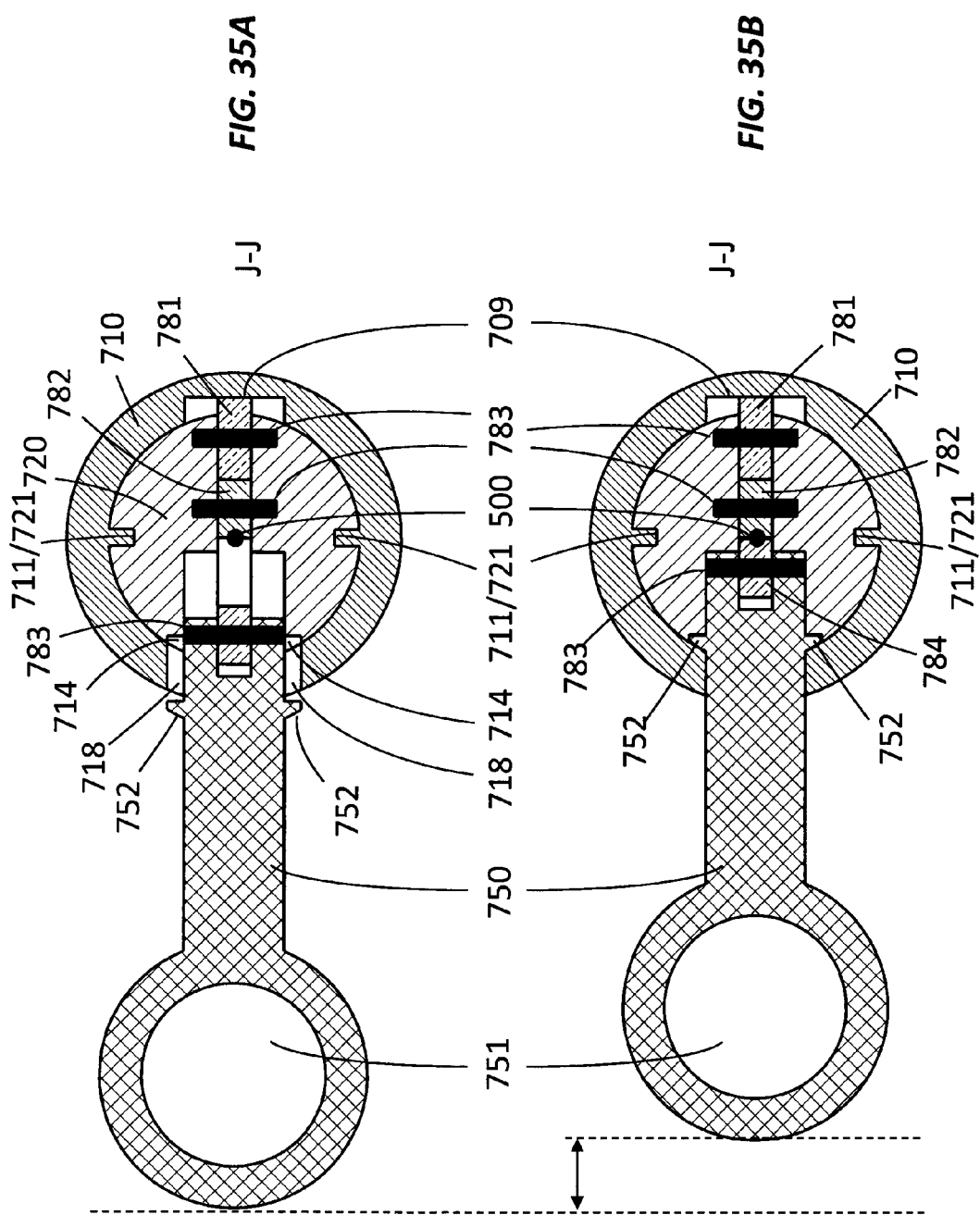

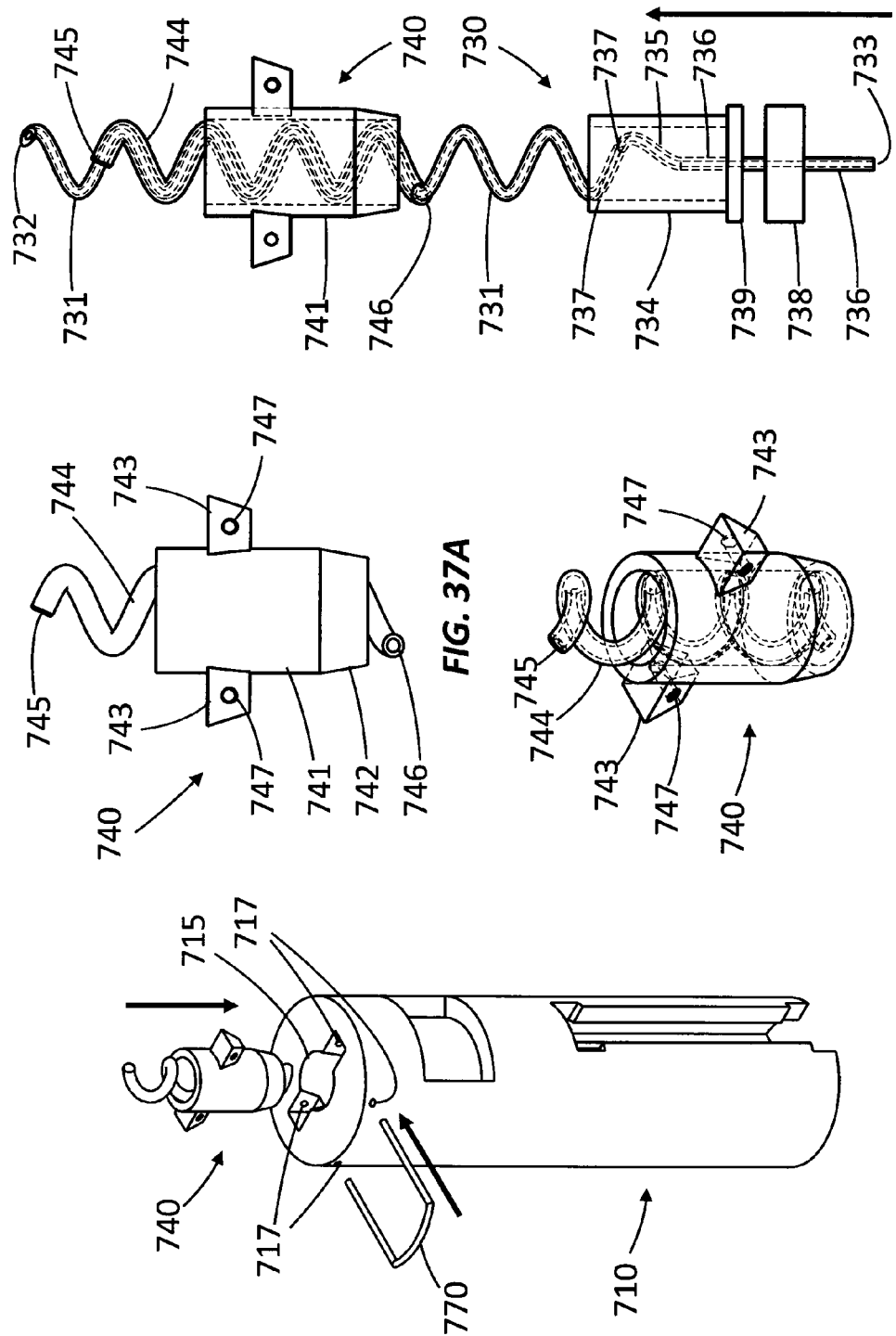

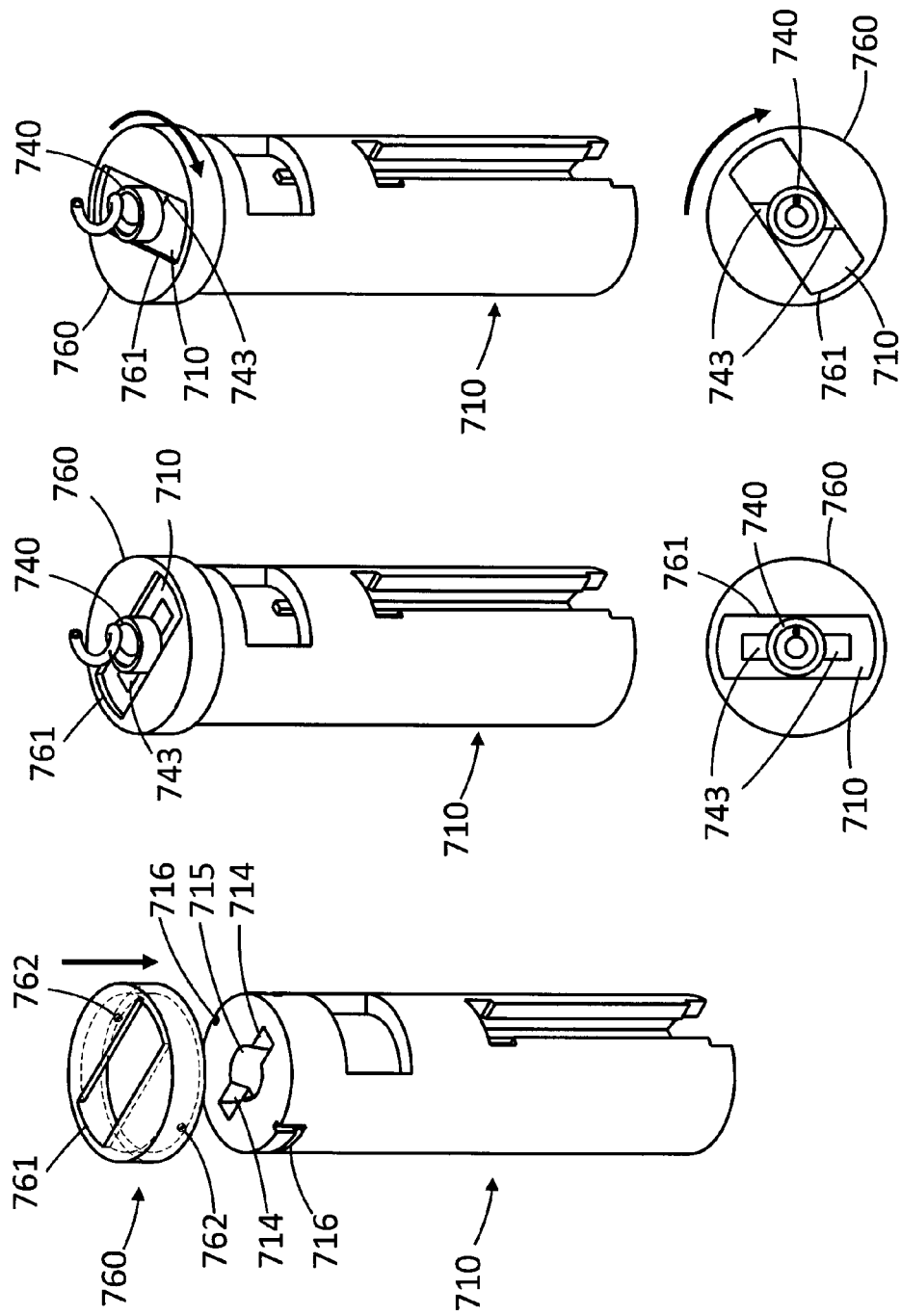

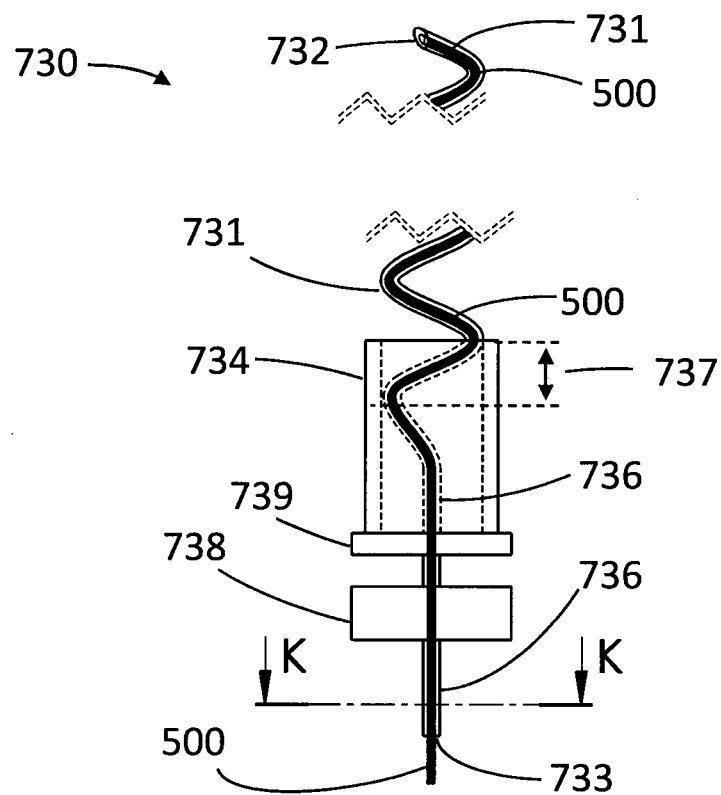
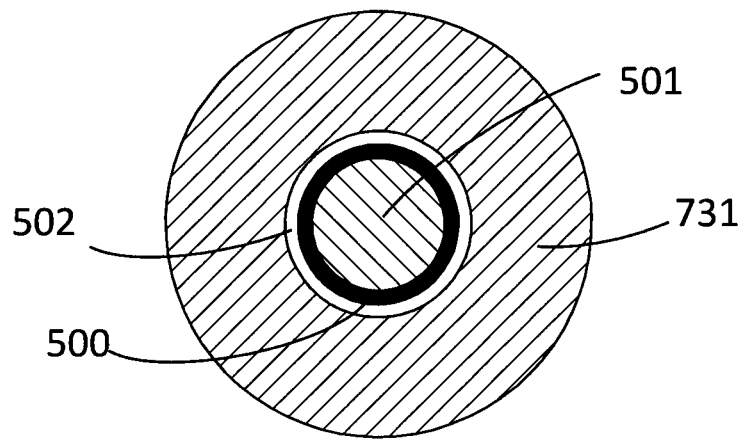
K-K
Scale 50 : 1
*FIG. 40*

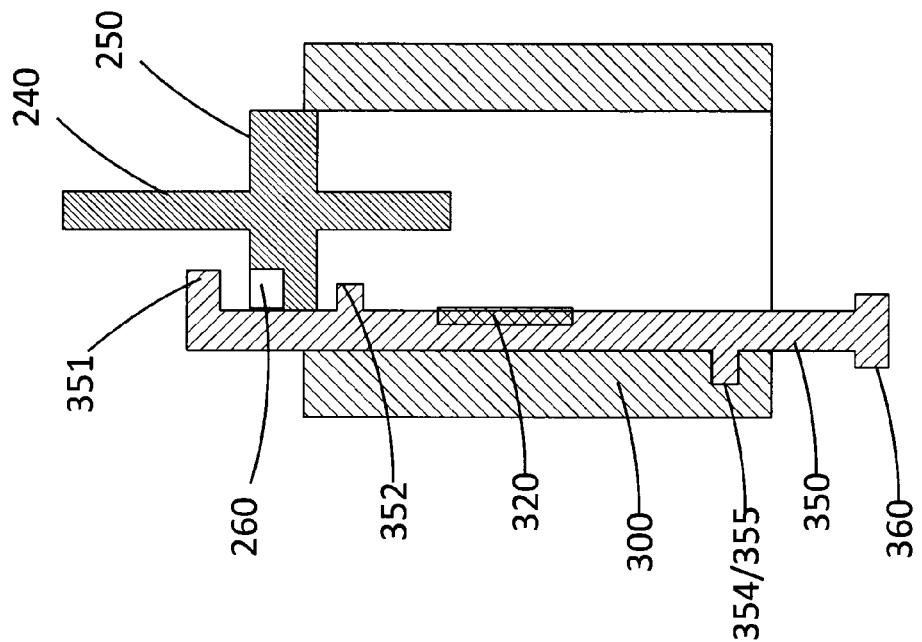
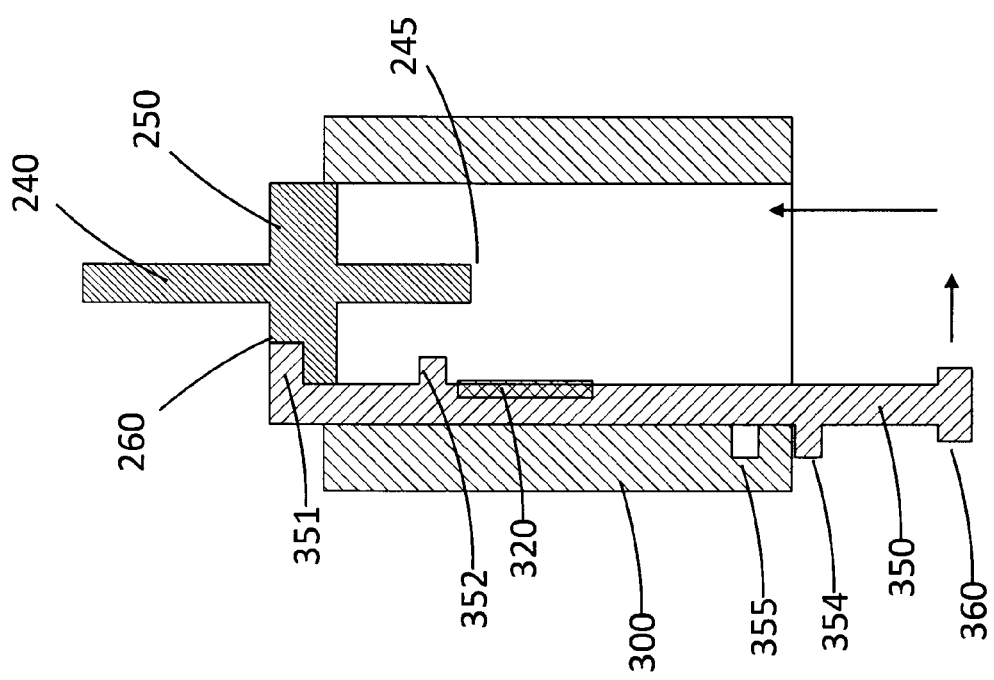
FIG. 41A
FIG. 41B

| Needle Gauge | Nominal Outer Diameter | | Nominal Inner Diameter | | Nominal Wall Thickness | |
|---|---|---|---|---|---|---|
| | Inches | Mm | Inches | Mm | inches | mm |
| 11 | 0.12 | 3.048 | 0.094 | 2.388 | 0.013 | 0.33 |
| 12 | 0.109 | 2.769 | 0.085 | 2.159 | 0.012 | 0.305 |
| 13 | 0.095 | 2.413 | 0.071 | 1.803 | " | " |
| 14 | 0.083 | 2.108 | 0.063 | 1.6 | 0.01 | 0.254 |
| 15 | 0.072 | 1.829 | 0.054 | 1.372 | 0.009 | 0.229 |
| 16 | 0.065 | 1.651 | 0.047 | 1.194 | 0.009 | 0.229 |
| 17 | 0.058 | 1.473 | 0.042 | 1.067 | 0.008 | 0.203 |
| 18 | 0.05 | 1.27 | 0.033 | 0.838 | 0.0085 | 0.216 |
| 19 | 0.042 | 1.067 | 0.027 | 0.686 | 0.0075 | 0.191 |
| 20 | 0.03575 | 0.9081 | 0.02375 | 0.603 | 0.006 | 0.1524 |
| 21 | 0.03225 | 0.8192 | 0.02025 | 0.514 | " | " |
| 22 | 0.02825 | 0.7176 | 0.01625 | 0.413 | " | " |

FIG. 43

HELICAL INSERTER

CROSS REFERENCE TO RELATED APPLICATIONS

This application is the National Stage of International Application No. PCT/IB2011/002878, filed Nov. 30, 2011, which claims benefit under 35 USC § 119(a), to U.S. provisional patent application Ser. No. 61/417,937, filed Nov. 30, 2010.

COPYRIGHT & LEGAL NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. Further, no references to third party patents or articles made herein are to be construed as an admission that the present invention is not entitled to antedate such material by virtue of prior invention.

BACKGROUND OF THE INVENTION

This invention relates to a device for inserting a flexible member into a living body, more particularly, for inserting a flexible member through a helically formed hollow needle.

A flexible, electrically conductive member is often used as an electrode for Functional Electrical Stimulation. Such member may be a regular electrode, a shape memory alloy or an electroactive polymer. Needle insertion into soft tissue is probably the most common surgical procedure for either therapeutic drug deliver or tissue sample removal from deep within the body. Hollow needles can also be used to implant electrodes or other members which fit through the lumen. Such needles are predominantly straight. For some procedures, needles can be bent in a preferred way, however, there are far fewer implanting procedures which involve helices. Devices and methods for medical inserting procedures, which make use of the helix, are known in the prior art. For example, tips of cardiac electrodes are often formed as a helix for the purpose of anchoring one end to a muscle of the heart, for example, the myocardium. The helix/coil at the end of the electrode is used to screw and hold it in place. There are several procedures which rely on the same basic tissue anchoring mechanism to affix an inserted member to a specific tissue location. There are even endoscopical procedures, such as described in U.S. patent application Ser. No. 12/363,137, to Fox, entitled SURGICAL DEVICE, the content of which is incorporated herein by reference thereto, which, during surgery, only temporarily fixes an overtube to an organ wall using a helical anchoring mechanism.

Still further, there are procedures involving helical needles for the delivery for fluids. As an example, in U.S. Pat. No. 7,309,325 to Mulier et al, entitled HELICAL NEEDLE APPARATUS FOR CREATING A VIRTUAL ELECTRODE USED FOR THE ABLATION OF TISSUE, the content of which is incorporated herein by reference thereto, a helical needle is used to deliver a conductive fluid to a target site.

U.S. patent application Ser. No. 11/834,186, to Rioux, entitled CORKSCREW HELICAL INSERTER PORT, the content of which is incorporated by reference hereto, describes a method and a device for inserting a helical member into a septum for injection or extraction of fluid therein. The device may include a handle having an actuator lever rotatably coupled thereto. The device may also include a helical member which has a tissue piercing distal tip. The helical member is coupled to the handle via a linkage operating so that, as the actuator lever is rotated in a first direction relative to the handle, the helical member is rotated and moved distally to screw into tissue along a substantially helical path.

In U.S. Pat. No. 7,637,918, to Dant, entitled HELICAL SUTURING DEVICE, the content of which is incorporated by reference hereto, a helical hollow needle is used to helically insert a suture, which is retrieved at one end with a straight retriever along the axis of the helix.

Nevertheless, what is needed is an inserter, which can insert an electrode or a shape memory alloy into soft tissue through a helical hollow needle along a helical punctured pathway and do so quickly, safely and precisely, so as to minimize or eliminate drift or wander. Furthermore, if the member inserted must maintain a desired orientation with respect to the tissue of the punctured pathway, a mechanism is needed which ensures precise delivery without twisting of the member, as the needle withdraws from the pierced tissue.

Still further, what is needed is a method of inserting a flexible member in soft tissue precisely along a predefined helical path, with a mechanism, which can push said member out of a helical hollow needle when withdrawing it, with said member maintaining its orientation with respect to the tissue.

SUMMARY OF THE INVENTION

A method and apparatus for inserting inserts helically into soft tissue is provided. The inserter is made up of a housing assembly, a hollow helical needle guide; and a needle insertion drive. In its basic form, the apparatus includes a housing assembly, a hollow helical insert guide, a helical insert drive and a guide removal device. The hollow helical insert guide is held in functional relationship by the housing assembly and is adapted to be loaded with the insert for helical transport therewith into the soft tissue. The helical insert drive drives the helical insert guide in rotation and translation into the soft tissue. When an insert is present within the insert guide, the guide removal device removes the insert guide while leaving the insert in its intended implant location in the soft tissue.

In one embodiment, the helical insert drive includes a matched first and second hypoid gear. The first hypoid gear wheel is affixed to the proximal side of the helical needle and held in axial position through the housing assembly for rotational insertion into the soft tissue. The second hypoid gear wheel is matched to the first hypoid gear wheel and held in axial position through the housing assembly. The second gear wheel drives an implantable member insertion mechanism. The insertion mechanism is adapted to insert an implantable member by its being transported into its final position in soft tissue by the hollow helical needle into the soft tissue as the hollow helical needle is driven in rotation and translation into the soft tissue.

An object of the invention is to provide a method and apparatus to insert a flexible member helically into soft tissue in a fast in a precise and safe way.

Another object of the invention is to provide a method and apparatus for inserting an implantable member helically into soft tissue, thereby better fixing the implantable member through the geometrical structure of the helical pathway in the soft tissue, when such tissue is deformed. For deformable body sections, especially muscles, tissue incompressibility is commonly assumed, as the tissue is highly aqueous. As a muscle contracts, it gets compressed, which means shorter along the axis of the muscles fiber orientation and wider viewed from a perpendicular plane according to Poisson's ratio. A helically implanted flexible member can behave in a same manner, by substituting diameter of the helix for length/height along its axis, when the muscle contracts and expands. This is why a flexible, but non-elastic member like a stranded cable electrode may be implanted into these body sections, which undergo a relatively large change in length between septum access and distal end of the member.

Another object of the invention is to provide an improved method of helical insertion of a flexible member, which allows planning of a precise pathway regarding its orientation and position inside the tissue and ensuring a piercing and insertion exactly along this desired pathway in a safe and reliable manner. It is therefore also possible to plan and pierce a pathway through the tissue having a desired orientation of the punctured pathway at a certain distance. As an example, the helical puncture pathway of the member may be through two muscles in contact with each other where it is required that the pathway crosses these muscle layers is in a desired orientation, because of specific deformations and displacements occurring at the muscle layer boundary.

Another object of the invention is to provide a method of helical inserting with superficial tissue layers not helically pierced providing means to only helically pierce posterior layers.

BRIEF DESCRIPTION OF THE DRAWINGS

FIG. 3A is a front view of the proximal housing fully injected

FIG. 3B is a longitudinal cross sectional view B-B as indicated in FIG. 3A through distal and proximal housing, mechanism inside excluded from cross section, mechanism closed and activated like when fully injected before withdrawal of proximal inserter.

FIG. 3C is a longitudinal cross sectional view C-C as indicated in FIG. 3B, mechanism closed

FIG. 5A is a front view of the needle part.

FIG. 5B is a perspective view of needle part.

FIG. 5C is a perspective view of needle part

FIG. 6A is longitudinal cross sectional view E-E as indicated in FIG. 5A through needle drive crown wheel.

FIG. 6B is a longitudinal cross sectional view E-E of an alternative solution for needle drive wheel, longitudinal cross section through needle drive crown wheel with helical needle bent toward center inside wheel.

FIG. 9 is a perspective view of an exemplary alternative wedge triggering mechanism with front shaft 67 and rod 55 semi-transparent, without driven wheel.

FIG. 10 is a perspective view of a wedge triggering mechanism with only one shaft part (68) shown.

FIG. 12A is a front view of the mechanism in a deactivated state.

FIG. 12B is a front view of the mechanism in an activated state.

FIG. 13a is a front, oblique, partially disassembled view of an alternate, screw thread version of the invention.

FIG. 13b is a front, oblique, assembled view of an alternate, screw thread version of the invention.

FIG. 14 is a perspective view of the alternate embodiment of the invention.

FIG. 15a is a perspective view of the distal housing of the alternate embodiment of the invention.

FIG. 15b is a perspective view of the distal housing of the alternate embodiment of the invention, with the housing tilted backward to expose a portion of the inner thread.

FIG. 16a is a cross sectional, perspective view F-F, as indicated in FIG. 15A, of the distal housing of the alternate embodiment o the invention.

FIG. 16b is a cross sectional, perspective view G-G, as indicated in FIG. 15B, of an alternate distal housing of the alternate embodiment of the invention.

FIG. 17a is a cross sectional view F-F, as indicated in FIG. 15A, of the distal housing of the alternate embodiment o the invention.

FIG. 17b is a cross sectional view G-G, as indicated in FIG. 15B, of an alternate distal housing of the alternate embodiment of the invention.

FIG. 20a is a side view of the needle and gear assembly used in the alternate embodiment of the invention.

FIG. 20b is an oblique, side view of the needle and gear assembly used in the alternate embodiment of the invention.

FIG. 20c is an oblique side view of the needle and gear assembly used in the alternate embodiment of the invention, tilted forward.

FIG. 21a is a cross sectional H-H, as indicated in FIG. 20A, partial side view of the needle and gear assembly which may be used in the alternate embodiment of the invention.

FIG. 21b is a cross sectional H-H, partial side view of the needle and gear assembly of a preferred embodiment used in the alternate embodiment of the invention.

FIG. 24a is a cross sectional, side view of the needle and gear assembly used in the alternate embodiment of the invention, showing an open position of the inserter mechanism of the invention.

FIG. 24b is a cross sectional, side view of the needle and gear assembly used in the alternate embodiment of the invention, showing a closed position of the inserter mechanism of the invention.

FIG. 25a is a close up, oblique, cross sectional view of the needle and gear assembly used in the alternate embodiment of the invention showing a open position of the triggering mechanism of the invention.

FIG. 25b is a close up, oblique, cross sectional view of the needle and gear assembly used in the alternate embodiment of the invention showing a closed position of the triggering mechanism of the invention.

FIG. 26a is a close up, oblique, partially assembled view of the needle and gear assembly used in the alternate embodiment of the invention showing an open position of the triggering mechanism of the invention.

FIG. 26b is a close up, oblique, partially assembled view of the needle and gear assembly used in the alternate embodiment of the invention showing a closed position of the triggering mechanism of the invention.

FIG. 27a is a close up, partially assembled view of the needle and gear assembly used in the alternate embodiment of the invention showing an open position of the triggering mechanism of the invention.

FIG. 27b is a close up, partially assembled view of the needle and gear assembly used in the alternate embodiment of the invention showing a closed position of the triggering mechanism of the invention.

FIG. 29a is a close up, oblique, cross sectional view of the needle and gear assembly used in the alternate embodiment of the invention showing the open position of the triggering mechanism of the invention.

FIG. 29b is a close up, oblique, cross sectional view of the needle and gear assembly used in the alternate embodiment of the invention showing the closed position of the triggering mechanism of the invention.

FIG. 30 is a close up, top, partially assembled view of the gear assembly used in the alternate embodiment of the invention showing a closed position of the triggering mechanism of the invention.

FIG. 34A-34D are a cross sectional views as indicated in FIG. 33B with the inserter at different positions with the corresponding transverse cross sectional view J-J as indicated in FIG. 33A through the mechanism in different positions.

FIGS. 35A and B are close up transverse sectional views of FIGS. 34A and C

FIG. 36 is a perspective view of a guide tube fixation.

FIG. 37A is a front view of an exemplary guide tube.

FIG. 37B is a perspective semi-transparent view of an exemplary guide tube

FIG. 38 is a front view semi-transparent of an exemplary guide tube and needle part FIG. 39A is a perspective view of the alternate guide tube fixation in separated state.

FIG. 39B is a perspective view and a top view of the alternate guide tube fixation in open state.

FIG. 39C is a perspective view and a top view of the alternate guide tube fixation in closed state FIG. 40 is a front view semitransparent of the needle part 730 showing the implantable member inside from tip of needle to the proximal needle orifice, and a cross section as indicated.

FIG. 41A is a schematic cross section of the activation mechanism with an integrated locking mechanism in a locked position.

FIG. 41B is a schematic cross section of the activation mechanism with an integrated locking mechanism in the unlocked position.

FIG. 43 is a specification table for typical needles of the prior art.

Figures 1A, 1B, 1C:
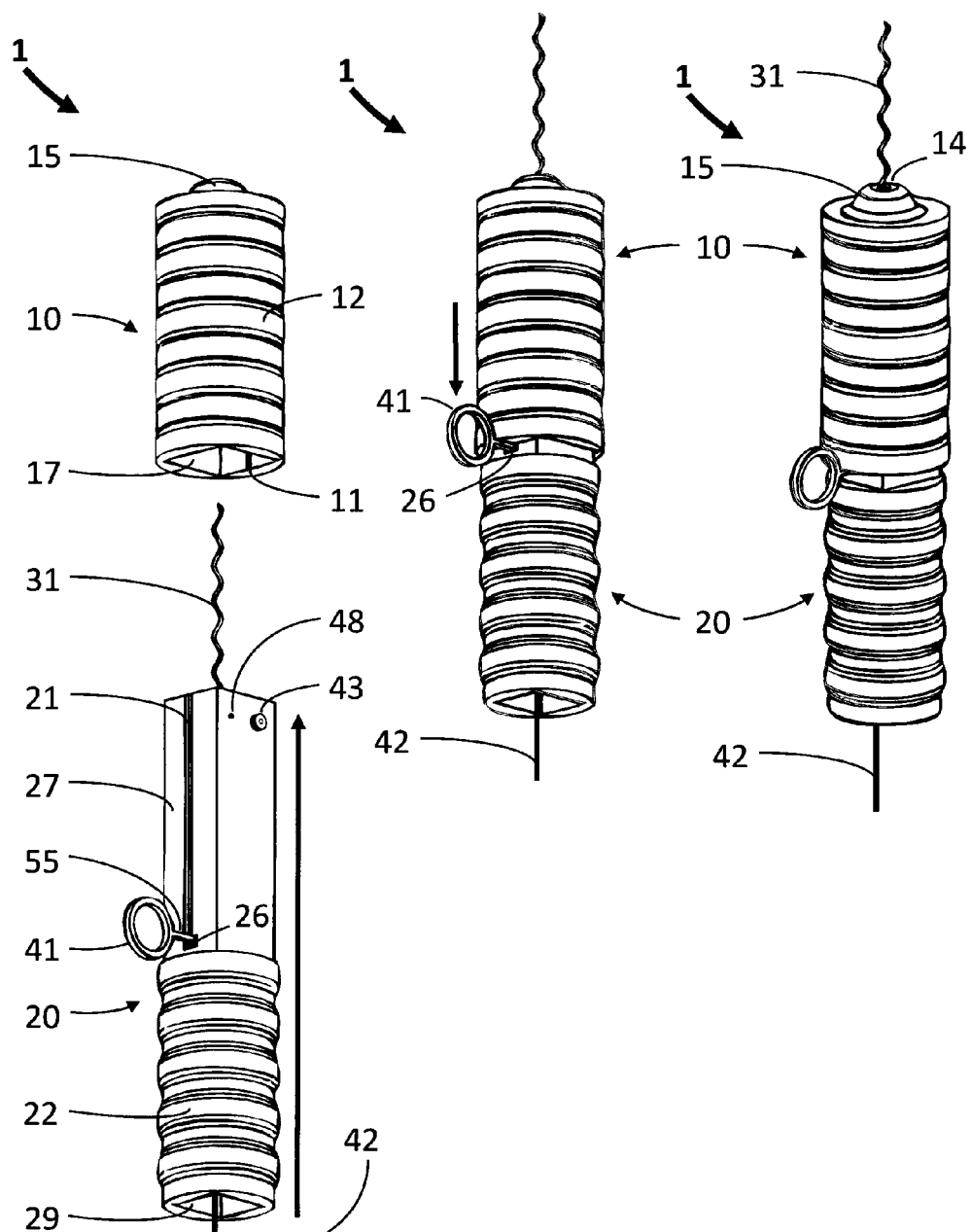
FIG. 1A is a perspective view of an exemplary injection assembly according to the present invention with distal and proximal housing separated.
FIG. 1B is a perspective view of an exemplary injection assembly according to the present invention with proximal housing inside distal housing (fully injected).
FIG. 1C is a perspective view of an exemplary injection assembly according to the present invention with proximal housing inside distal housing (fully injected).

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention. Furthermore, the terms 'first', 'second', and the like herein, if any, are used inter alia for distinguishing between similar elements and not necessarily for describing a sequential or chronological order. Moreover, the terms 'front', 'back', 'top', 'bottom', 'over', 'under', 'proximal', 'distal' and the like in the Description and/or in the claims, if any, are generally employed for descriptive purposes and not necessarily for comprehensively describing exclusive relative position. Skilled artisans will therefore understand that any of the preceding terms so used may be interchanged under appropriate circumstances such that various embodiments of the invention described herein, for example, are capable of operation in other configurations and/or orientations than those explicitly illustrated or otherwise described.

DETAILED DESCRIPTION OF THE PREFERRED EMBODIMENT

The following descriptions are of exemplary embodiments of the invention and the inventors' conception of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

A method and apparatus for inserting inserts helically into soft tissue, as well as an insert guide which optionally contains an insert, is provided. In its basic form, the apparatus includes a housing assembly, a hollow helical insert guide, a helical insert drive and a guide removal device. The hollow helical insert guide is held in functional relationship by the housing assembly and is adapted to be loaded with the insert for helical transport therewith into the soft tissue. The helical insert drive drives the helical insert guide in rotation and translation into the soft tissue. When an insert is present within the insert guide, the guide removal device removes the insert guide while leaving the insert in its intended implant location in the soft tissue.

The hollow helical insert guide 31, 210 is held in functional relationship by the housing assembly wherein the guide is loaded with the insert 500 for helical transport therewith into the soft tissue. The helical insert guide drive is made up of components 13, 33, 43, 44, 49, 50; 100, 110, 220, 230; 250, 420, 470, 709, 734, 738, 739, 740, 781, depending on the embodiment. The guide drive drives the helical insert guide in rotation into the soft tissue. The guide removal device is made up of several components 13, 28, 33, 41, 43, 44, 45, 49, 50, 51, 52, 53, 54, 55; 250, 420, 430, 470; 709, 781, 782, depending on the embodiment, which, when the insert 500 is present within the insert guide 31, 210, removes the insert guide while leaving the insert in its intended implant location in the soft tissue.

In an exemplary embodiment, the inserter 1 is made up of a housing assembly, a hollow helical needle; and a matched first and second hypoid gear. The first hypoid gear wheel is affixed to the proximal side of the helical needle and held in axial position through the housing assembly for rotational insertion into the soft tissue. The second hypoid gear wheel is matched to the first hypoid gear wheel and held in axial position through the housing assembly. The second gear wheel drives an implantable member insertion mechanism. The insertion mechanism is adapted to insert an implantable member through the hollow helical needle into the soft tissue after the hollow helical needle has been rotationally driven into the soft tissue.

As can be appreciated even by those of extraordinary skill in the art, inserting a member helically through a helical hollow needle is more difficult than doing the same with a straight needle in at least three ways, thus presenting the need to develop solutions beyond the skill of those of ordinary skill in the art. These three aspects are described below.

First, in order to gain an advantage of the invention, each puncture pathway made by a helical needle is oblique in relation to an outer surface of the septum. These diagonal puncture pathways wrap around the injection/withdrawal axis enhancing the ability of the implanted member to deform and elongate equally with the tissue. The path the needle cuts through tissue can be influenced, because both a rotational and a simultaneous linear motion of the needle are required. Through altering the ratio of these two motions, the deformable tissue is either expanded or contracted when "screwing" the needle in the soft tissue. This has direct influence for resulting path and endpoint inside the tissue. Therefore, it is not just the form of the helical hollow needle which influences the resulting path; the forces applied during insertion of the needle do as well. That's a crucial point, in order to ensure that the inserted member fits in its insertion position in length and orientation. Controlled insertion enables the planning of a desired path through tissue and guarantees predictable results.

Second, the needle must be forced to rotate about the axis to screw into tissue along a substantially helical path. During the inserting procedure, the member will be hanging out of the proximal aperture of the needle and then be rotated along the middle axis of the helix as the needle turns. Therefore the member cannot be affixed to a part which doesn't turn outside the proximal aperture of the helical needle as it would twist the member.

Third, once the desired location inside the tissue is reached and the orientation of the member inside the needle in relation to the tissue is correct, the member must now be pushed out as the needle is withdrawn. This is easier to do with a straight needle, because of lower friction forces (as compared to turning along a curvature) and no member deformation forces at the section of the needle, where the member moves from the center of the axis to the helical section. The needle will turn as it is withdrawn, but the member should only experience a linear push out force. In contrast with a straight needle, the length of the needle (=length helix) and the distance access/end point (height of helix) are different. A gearbox adjusts for that difference as it transforms the pull back movement into linear push out force, as the inserter is withdrawn.

Therefore, the insertion device provides three functions:
1. Rotation: for translating a linear motion into a circular motion, so that the hollow helical needle screws in and out along its helical path.
2. No Twisting: for free rotation of the implantable member outside the proximal aperture of the needle, during insertion of the needle.
3. Linear push out: for transforming the pull-back motion when withdrawing the needle into a linear push out force for the member inside the hollow needle. The difference in length of the helix and linear pull back distance (=height of helix) is matched through a gearbox with precise gear ratio.

Figure 42:
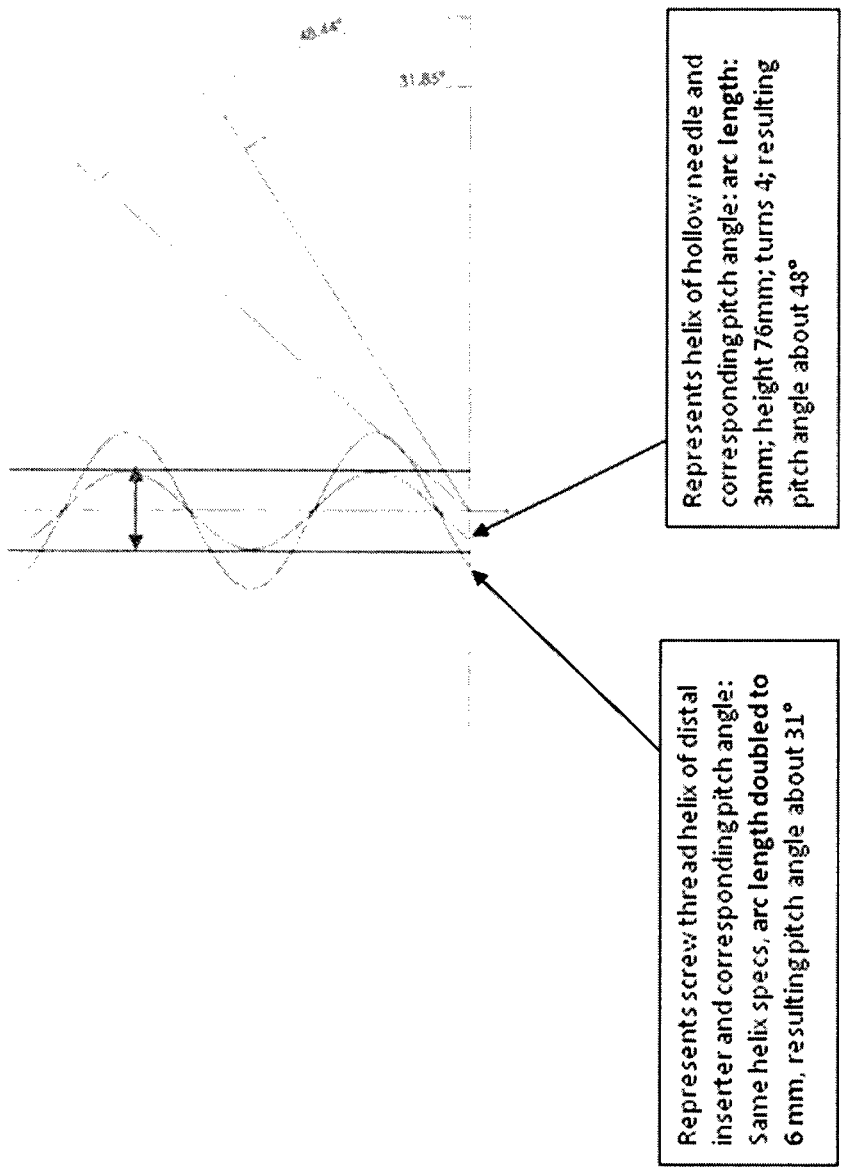
FIG. 42 is a schematic diagram illustrating screw thread helix of distal inserter and corresponding pitch angle compared to helix of hollow need and corresponding pitch angle.
Figure 44:
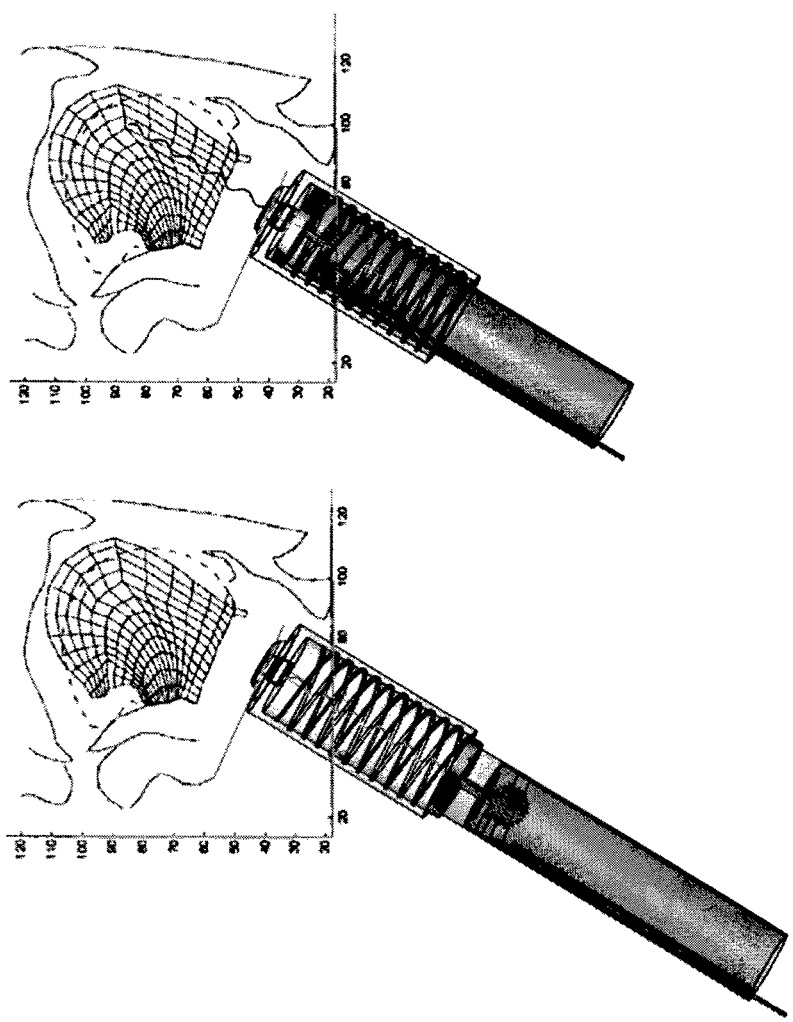
FIG. 44 is an exemplary drawings showing use of the inserter in a submental approach for the treatment of obstructive sleep apnea.

Before Inserting: Planning of Surgery and Needle (Helix) Determination:

Referring to FIGS. 42 to 44, as opposed to a straight needle, where only length and diameter of the needle (needle gauge) have to be chosen, inserting a helical needle needs further determination: the helix needs to be specified, and this influences the surgery as well as the result. Collection of fundamental patient data and planning of surgery is therefore required. The following steps should therefore be performed:
1. Gather Data: CT or MRI of body section, if necessary with tissue in a deformed state 2. Estimate/Calculate (iterative):
   Point of access, end point, effects overall height of helix needle
   Desired path
   Check for obstacles (veins, arteries, nerves) effects desired path for surgery
   Elongation and deformation extremes estimate effects arc length, pitch, No. turns effects desired path regarding deformation of member
3. Determine needle to be used: arc length, pitch, no. of turns Needle Specifications: Range of Values for the Treatment of Obstructive Sleep Apnea with Submental Inserting:

| | |
|---|---|
| Height of helix: 50 mm-100 mm | typical: 75 mm |
| Arc length: 1.5 mm-15 mm | typical: 3-4 mm |
| Turns: 3-7 | typical: 4-5 |
| Pitch (resulting: height/turns) 7 mm-33 mm | typical: 15 mm |
| Needle gauge: 14-21 | typical: 16-17 (with increased wall thickness for load) |

Hypodermic needles are available in a wide variety of outer diameters described by gauge numbers. Smaller gauge numbers indicate larger outer diameters. Inner diameter depends on both gauge and wall thickness. There is another gauge system: The French scale or French gauge system (most correctly abbreviated as Fr, but also often abbreviated as FR or F) is commonly used to measure the size (diameter) of a catheter. 1 Fr=0.33 mm, and therefore the diameter of the catheter in millimeters can be determined by dividing the French size by 3: D (mm)=Fr/3 or Fr=D (mm)×3. An increasing French size corresponds to a larger-diameter catheter. This is contrary to needle-gauge size, where the diameter is 1/gauge, and where the larger the gauge the narrower the bore of the needle.

Figure 45:
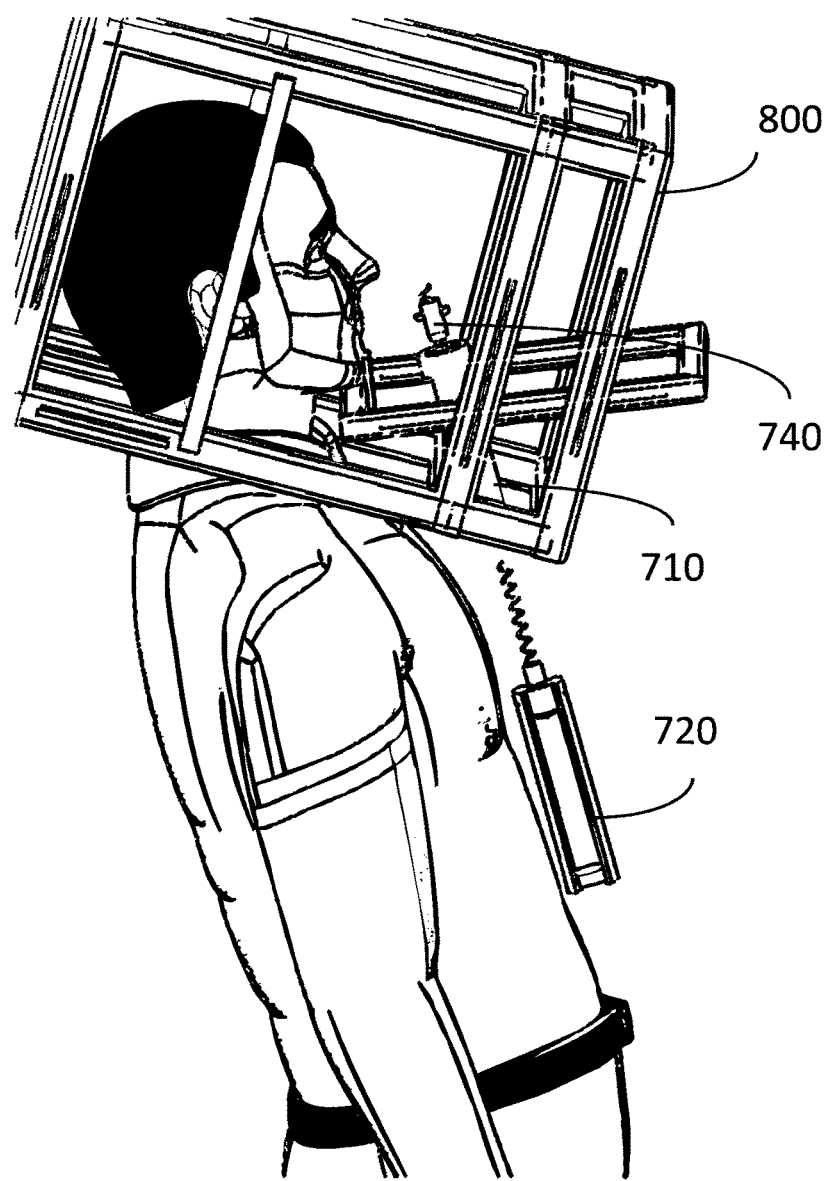
FIG. 45 is a schematic view of the fixator for fixing the patient and inserter of the invention.

Referring to FIG. 45, exemplary drawings show use of the inserter in a submental approach for the treatment of obstructive sleep apnea.

For use of the invention in the treatment of Sleep Apnea, the following steps are performed:
1. Place head in fixed position using a fixator 800 (See FIG. 45) controlled and stable position)
2. Collect data of tongue in rest position and other deformation extremes (CT better than MRI [time]), create 3D model
3. Determine needle size
4. Put inserter in position or mount on rack (precise access through tissue in 3 dimensions)
5. Confirm desired position of tongue and head with scan before inserting (CT or Ultrasound)
6. Apply mechanism; may be verified/controlled with ultrasound during surgical procedure, but no CT (due to possible radiation of surgeon)
7. Confirm position with scan (CT or Ultrasound)

Utilization of Drive Inserter

As shown in FIG. 1A-1C, an embodiment for a flexible member helical drive inserter includes a distal housing 10 with a rack inside, a left-handed helical hollow needle 31 and the proximal actuator housing 20 with a mechanism inside, driven by the main drive pinion 43. The implantable member 42 is already inside the hollow needle part, just below the tip of the needle 37.

The distal inserter housing 10 is either held with one hand or optionally mounted on a rack, for securely attaching the assembly in a desired location on or near the body to provide a stable base on which to rest. Once the distal housing 10 is orientated with regard to the tissue access point and all three axes, the proximal actuator housing 20 is pushed inside the distal 10, as indicated by the arrow in FIG. 1A. This rotates the needle 31 and pierces and threads it inside the tissue along a substantially helical path. When the proximal housing 20 has been pushed fully inside the distal housing 10, the inserting mechanism activator rod 55 is automatically pressed down by the edge of the distal housing 10, as indicated by the small arrow in FIG. 1B; due to the adapted position of rod 55 and aperture 26. This activates the flexible member push out mechanism inside the proximal actuator 20. Now, while the proximal actuator housing 20 is pulled out of the distal housing 10, the inserting mechanism activator rod 55 must remain in a pulled position (mechanism active) and the implantable part 42 is automatically pushed out of the helical hollow needle 31; as it retracts from the pierced tissue. The forefinger keeps the trigger 41 in that position and it is of help withdrawing the proximal actuator 20. Once the actuator 20 reaches the end of the distal housing 10, the tip 37 of helical needle 31 is already outside the tissue. The inserting mechanism activator trigger 41 is now pushed towards the distal housing 10 (initial position) to disengage the push out mechanism. Now, the distal housing 10 may be slightly pulled back to open up a gap between skin/tissue and the boss 15 of the inserter. Then the implantable member 42 may be grabbed by fingers or a clamp between the needle orifice port 14 and skin/tissue, to cautiously pull the remainder of the member 42 through the disengaged inserter/needle 20, 31 and out. This finishes the helical inserting procedure for a flexible member 42 into soft tissue.

Distal Housing 10

The functions of the distal housing 10 are as follows:
1. Hold the inserter in position regarding tissue access point and path of the needle 31.
2. Provide stability during the inserting procedure.
3. Drive the whole mechanism inside the proximal housing 20 (turning of needle and push out of member) by acting as counterforce.

Referring again to FIG. 1A, 1B, 1C, the distal housing 10 is a hollow cylinder, closed on top (distal); open at the bottom (proximal). The top of the inserter, which is in contact with skin, may include a boss or bulge 15 for better skin contact and tension at the septum access point of the needle. On top of the boss 15 is the needle orifice port 14, with a minimal diameter equal to the diameter of the whole helical needle 31. It maybe of slightly conical shape to guarantee that the needle tip 37 always enters the port 14 and no damage to the tip takes place when assembling the distal housing 10 with the proximal housing 20. Note that in order to improve retention and control of the needle 31 at the distal end, an insert guide having a helical port formed therein (not shown but similar to the guide 740 except that it is free to rotate in the orifice port 14), may be rotatably inserted into the port 14. The outer hull of the distal inserter 10 may have a textured, structured or grooved surface to provide good grip for the handhold 12. Anchor arms or some sort of rack could optionally be used, if the inserter should be securely attached at or near the body.

Figure 4A:
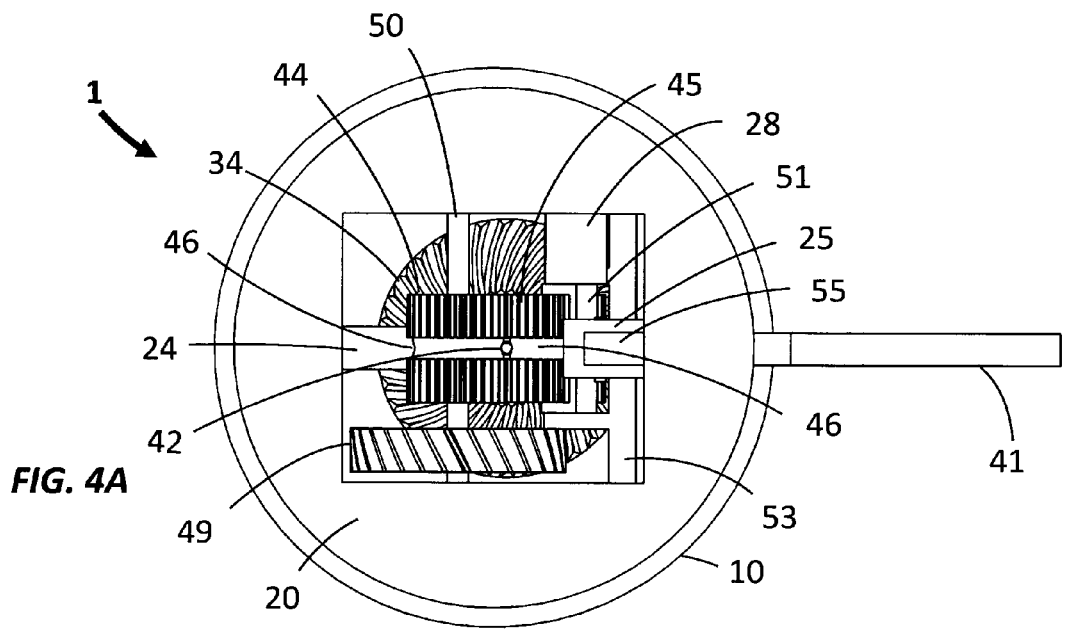
FIG. 4A is a bottom view of an exemplary injection assembly, mechanism closed.
Figure 4B:
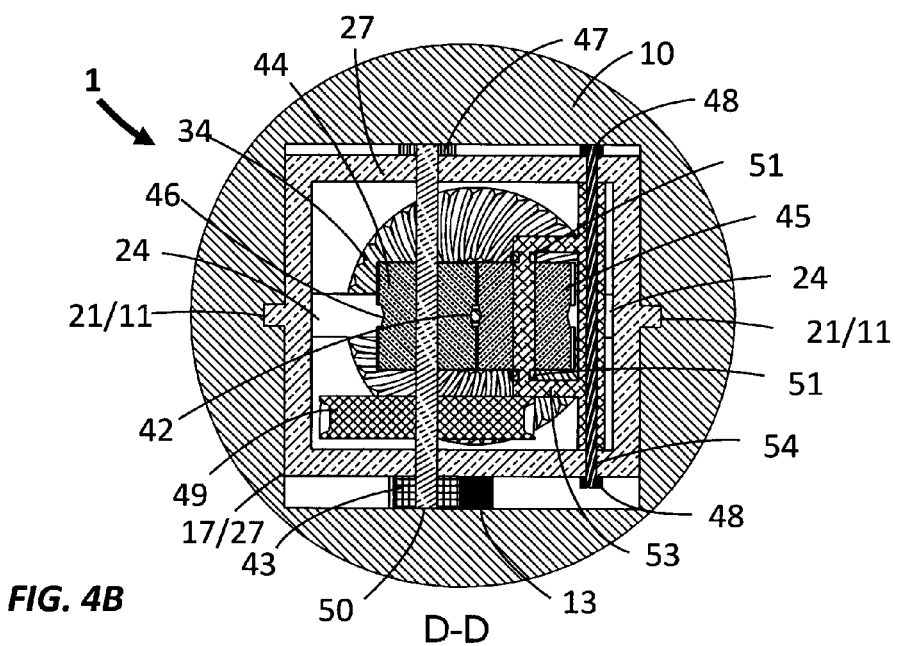
FIG. 4B is a transverse cross sectional view D-D as indicated in FIG. 3B through the mechanism in closed position.

Referring to FIGS. 1A, 2A, 2B, 3A, and 3B and cross-section FIG. 4B, the inner profile 17 of the distal housing 10 could have many different forms; it must only ensure that the proximal actuator 20 can glide in/out, so that the rack 13 inside the distal inserter 10 is in good contact with the main drive pinion 43. In an exemplary assembly, the inner profile 17 of the distal housing 10 is of rectangle shape, as well as the outer distal profile 27 of the proximal actuator 20. The inner profile of the distal housing 17 has two cut-in sliding guides 11 for the proximal actuator 20, which has corresponding sliding bars 21 on a distal side 27. The rectangle shape of distal housing and distal side 17 and 27, respectively, are only of the same length on the sliding guide side. The sliding guides restrict movement with respect to the other axis. On one side, there is extra space required for the pinion 43 and on the other side there may be hinge pins 47/48, which require extra space as well (as can be seen in the transversal cross-section of FIG. 4B).

A solution without sliding guides would require the inner profile of the distal housing 17 and the distal profile of the proximal inserter 27 to be almost congruent, which requires that no hinge pins be cut in rack (not shown in drawings).

An exemplary cross-sectional view for profile without sliding guides and hinge pins is found on page 18 of the priority application incorporated by reference hereto.

At the bottom (proximal) end of the distal housing 10, an optional stop block prevents the proximal actuator 20 from coming out of the distal inserter housing 10, e.g. at the end of the rack (not shown in the drawings).

The Helical Hollow Needle Part/Helical Insert Guide 30

The functions of the helical hollow needle part 30 are as follows:
1. Pierce tissue helically
2. Make helical needle rotatable and drivable
3. If the member is not already in the needle when the needle is driven into soft tissue, provide an aperture for pushing the member into and through needle.

Bevel tip design influences forces and deformations on the pierced tissue and this influences the resulting path. There already exists fundamental scientific knowledge regarding that matter and how to simulate the behavior. As shown in FIGS. 5A and 5B, the sharp tissue piercing distal tip 37 includes an aperture which opens a lumen extending through the needle to the proximal needle aperture 39. The inner diameter is constant and determined by the diameter of the flexible implantable member 42. The left-handed helix of the needle is determined using the process already explained. Regarding the needle tip 37, there are numerous different tip designs available, in advanced medical applications predominantly laser cut, such as shown on page 19 of the priority application incorporated by reference hereto. The bevel tip 37 is preferably oriented to the inside of the helix as indicated in FIG. 5A to 5C.

Typically, the helical part of the needle is about 75 mm in height (length), arc length 3 mm, turns 5. This part of the needle must be outside the needle orifice port 14 of the distal housing 10 and will be fully injected into the tissue. As a result, the needle must be longer by the distance inside the inserter beginning from the orifice 14. A needle drive crown or hypoid gear 33 is affixed to the proximal side of the helical needle 31, with a gearing 34 at the bottom (proximal) to make the needle part 30 rotatable and drivable. At the proximal side of drive wheel 33, the needle needs to be a straight concentric tube 36, with an aperture 39, in which the member 42 will be pushed into to get it through the needle either before of after the insertion, or as a subsequent step to insertion of the needle 31. Fixing a wheel to the needle is a necessary step, because the needle itself is too small in diameter to directly cut in gearings into the tube section 36.

Referring now to FIGS. 5A to C, and FIG. 6A to 6B, proximal to the tissue penetrating helical needle section 31, the helix must change its path 32 to be concentric to the wheel 33 and from there on it is essentially a straight tube 36 along the axis of the helix. It should gradually deform from helix to straight with a steady path, so that the member inside glides and deforms smoothly. The question is: is the wheel affixed before or after it is bent towards the center as can be seen in cross section FIGS. 6A and 6B. If the wheel 33 is made of metal, a hole needs to be drilled in the center, then the wheel 33 must be pulled over the tube section 36 and (for example, laser) welded to it (FIGS. 5 & 6A, cross section E-E). If the wheel 33 is made of hard plastic, helix-to-straight section 32 could be inside the wheel 33 which would help fix the needle to the wheel (FIG. 6B).

A helical needle 31 is relatively simple to produce: a regular straight hollow needle made of e.g. a conventional 304 SS is helically bent cold worked and then heat treated. However, today, there are high performance alloys like e.g. "JAVELIN" (available from Creganna Inc, of Cambell, Calif.) used in medical applications, which offer excellent shape set resilience, greater material hardness, higher column strength and superior resistance to damage. The result is a smaller diameter of needle due to decreased wall thickness. The desired needle gauge is about 16, nominal outer diameter 1.651 mm (about 5 French scale). Thin-wall needles have identical outer diameters but larger inner diameters for a given gauge, thus a gauge 17 (1.473 mm, about 4 French scale) would suffice. Since forces applied to the helical needle differ significantly from those applied to straight needles, the wall-thickness must be increased. The wall thickness could even be gradually increased from tip 37 to the force exerting wheel 33 (not shown in drawings). This may be fabricated through a progressive extrusion process or by locally grinding the exterior of a tube blank before being formed into a helix. As the needle pierces the tissue, friction forces between needle and tissue may deform the tissue slightly, which would influence and potentially cause the needle to deviate from its intended helical pathway. That needs to be accounted for, if necessary, through the transmission ratio (to expand or contract tissue). If it is desired to minimize friction force of the needle 31 penetrating the tissue, the outer hull of the needle could be coated with a fluoropolymer, which would result in extremely low friction forces; for example spray-coating a thin layer of ETFE after the heat treatment of the helically bent needle.

The wheel 33 serves as crown wheel with right hand hypoid gearing 34 to drive/rotate the needle, which is driven by the left hand hypoid gear pinion 49. The distal side of the wheel 33 is a smooth surface, which is used as one side of a sliding contact together with the proximal actuator top 23, which has a hole for the needle. (FIG. 5C) At the proximal side of the wheel 33, the gearings 34 require extra distance to the needle bushing beam 24, which serves as bushing for the proximal tube section 36 of the needle to run through. It is achieved through an elevated sliding contact 35. Top sliding contact 23 (for FIG. 6A with or for FIG. 6B without bushing) and needle bushing beam 24 provide a confined space for the needle drive wheel 33. Friction forces are low by virtue of an adequate combination of materials.

Proximal Actuator Housing 20

The functions of the proximal actuator housing 20 are to act as a:
1. Casing/housing for the helical needle and the mechanism which drives it
2. Casing for the flexible member injection mechanism
3. Actuator for the whole helical inserter: pushing the needle into the tissue and rotating it to screw in along a substantially helical path and activating/driving the member injection mechanism The proximal actuator 20 has two different sections: the distal profile 27 and the cylindrical shaped proximal handhold 22; which may have a structured, grooved or otherwise textured surface for good grip. The bottom (proximal) end of the inserter 29 is open, such that the implantable member 42 can hang out and rotate freely during helical tissue penetration of the needle 31 (to avoid twisting) and move through the whole inserter, when pushing it out (member 42 not on spool). Inside the distal section 27 is the inserting mechanism 40.

The Drive Inserter Variant:

Referring again to FIG. 2B, the rack 13 drives the pinion 43, which is outside the distal profile 27 of the proximal actuator 20. Referring to FIG. 3A-3C, the pinion 43 is affixed to the shaft 50 running through the whole distal profile 27; on the pinion's opposing outer surface limited by a hinge pin or retaining device 47. The shaft 50 drives the whole needle part 30 as well as the member injection wheels 44/45, which push the implantable part 42 into the needle aperture 39 and subsequently out of it. The shaft 50 drives the needle drive crown wheel 33 through another pinion 49. The direction of the drive carried by the shaft 50 has to be transferred through 90 degrees to drive the needle crown wheel 33. But the drive wheel 44 on shaft 50 pushes the member 42 inside the aperture 39, which is also the center of the crown wheel 33 that needs to be driven by the same shaft. This makes a bevel gear design impossible; the drive wheel 44 on shaft 50 would intersect the member 42. The member injection drive wheel 44 needs to be dislocated, which also dislocates the whole shaft 50, puts it off-axis and results in a hypoid gear 34 to drive the needle part 30. A bevel gear solution is undesirable, because at least one extra gear is required, as well as an axis which does not intersect with the member 42 or aperture 39. A schematic representation of this arrangement is found on page 22 of the priority application incorporated by reference hereto.

It is known that hypoid gears are best for the applications requiring large speed reductions with non-intersecting shafts and those applications requiring smooth and quiet operation, such as a medical procedure. The left hand hypoid gear pinion 49 drives the right hand hypoid gearing 34 of the needle drive crown wheel 33. With that, the whole needle part 30 rotates and pierces the tissue along a helical path as the proximal actuator 20 is pushed in or pulled out of the distal inserter 10. Depending on required forces of transmission, the crown wheel and the hypoid gear may even be wheels without gear teeth. The member injection drive wheel 44 together with the driven wheel 45 push the implantable member 42, which is already inside the needle just below the tip 37, into the proximal hollow needle aperture 39, through the whole needle 31 and out at the distal needle tip side 37 when withdrawing the inserter. With only one shaft 50, the gearbox drive transmission must precisely match for two separate gear ratios simultaneously, in the following manner:

1. The rotation of the helical hollow needle must be matched to the linear push-in/pull out distance such that the pierced tissue isn't expanded or contracted, and 2. The gear transmission for the flexible member injector wheels 44/45 must adjust for difference in the length of helical needle and linear pull back distance of the proximal actuator 20 to push the member 42 out as the needle retracts.

For driving the needle: the gear ratios of rack 13/main drive pinion 43 and hypoid gear pinion 49/crown wheel of the needle 34 must be adjusted.—what is needed is 1 rotation of needle per pitch of distance.

For the pushing out of the implantable member: the gear ratio of rack 13/main drive pinion 43 and the circumference of the drive wheel 44 must be adjusted.

This is an optimization problem: the helix specifications are given and both functions/mechanisms are interdependent through the shaft 50 (this will be considered mathematically later).

The difference between these two mechanisms is that the needle drive is always on, but the member push out is only needed while withdrawing the inserted needle. Furthermore, the same mechanism must ensure that the implantable member 50 cannot be twisted during the needle injecting procedure; consequently, the implantable member 42 should freely rotate inside the proximal actuator 20.

Push Out Mechanism & Activation

The simplest solution is to open up the space between the wheels 44/45 which push the member out. Because the drive wheel 44 is fixed to the shaft 50, the driven wheel 45 is moved. There are several appropriate mechanisms that accomplish this: move the driven wheel 45 away from the drive wheel 44, such that contact area of the wheel groove 46 between the wheels opens up for the member 42 and it is no longer pulled/pushed or twisted by movements of the proximal actuator 20. The drive wheel 44 will still turn, but with no effect to the member. Because the member 42 is flexible, the wheels need to be as close as possible to the aperture 39, that the member cannot kink when pushing it in. These wheels will be deep inside the proximal housing 20; which itself is inside the distal housing 10, by the time the mechanism needs to be activated (like in FIG. 3). The distal housing 10 however should not have a cut-open section on one side to push the driven wheel 45 in with a button-like mechanism; this would negatively impact usability because the hands holding the two inserter parts 10/20 would have to move over each other.

It is preferred to have a trigger, which can be pulled over a short distance (<1 cm) to activate the push out mechanism. An assembly of rods make the activator trigger 41 easy accessible with one finger on the outside of the proximal actuator 20. Such a mechanism should guarantee that the trigger doesn't intersect the distal housing 10, as well as that the trigger can be used to better hold and pull the proximal actuator 20 out of the distal housing 10 (pull back/member push out move).

Figures 2A, 2B:
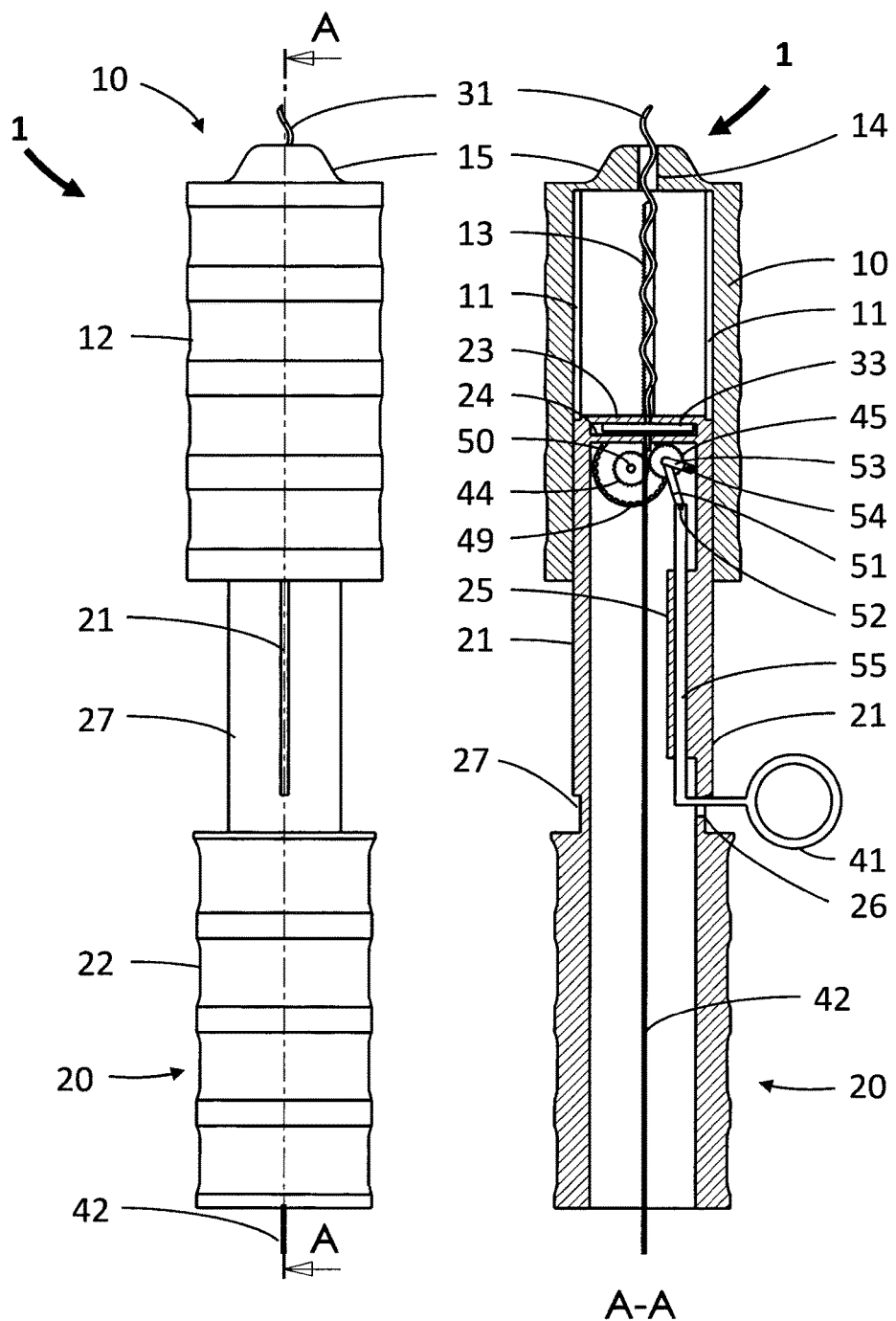
FIG. 2A is a front view of an exemplary injection assembly.
FIG. 2B is a longitudinal cross sectional view A-A as indicated in FIG. 2A through distal and proximal housing, mechanism inside excluded from cross section, member push out mechanism open (deactivated), like during inserting procedure of needle into tissue.

The driven wheel 45 can freely turn on a fork like axle 53, the driven wheel fork, which rotates about a fulcrum pin 54. It doesn't necessarily need to be a fork because a lever on one side could achieve the same result; but for equal force distribution, a fork is, for the moment, considered superior. The fulcrum pin 54 runs through the whole distal profile 27 of the proximal actuator 20, limited by hinge pins 48 outside the distal profile 27 (see FIG. 4B). In an alternative embodiment, the fulcrum pin 54 does not run through driven wheel fork 53, but rather, it runs through just one part with pins 54 on each side (not shown in drawings). Turning the fork 53 about the fulcrum pin 54 opens or closes the contact between driven wheel 45 and drive wheel 44. Both wheels in contact push the implantable member 42 into the proximal needle aperture 39. If the driven wheel 45 on fork 53 should open to the upside, the wheel groove 46 of the driven wheel 45 must pass the aperture 39 as the fork 53 rotates. Opening to the upside is preferred, because as the mechanism closes and the gearings of the wheel come into contact, it immediately creates a small pushing force on the member. The driven wheel 45 turns, when it closes, with the drive wheel 44 remaining stationary. This could be of use, for example if the distal part of the member 42 has an anchoring mechanism. The member would be pushed out for the small amount, such that the anchoring arms are already inside the tissue before the withdrawal process starts. This guarantees a more exact orientation of the tip of the member 42. During insertion of the needle, the fork is upward and wheels open, which opens a gap for the implantable member 42, in which it can rotate (FIGS. 2B and 2C). Pulling the activator trigger 41 turns the fork 53 to a horizontal position (FIGS. 3B and 3C, 4A and 4B, 7, 8) and the wheels are closed, in contact and the member push out activated. In an exemplary assembly, the rotation of the driven wheel fork 53 is distally limited by the needle bushing beam 24 and by a stop block 28 (see FIG. 3C, 4A) proximal. The stop block 28 limits the movement of the fork 53 to a stable horizontal position, as long as the rod/trigger 55/41 remains pulled. This is the reason why the rod 51 manipulating the driven wheel fork 53 is on the inner side of the fork (FIGS. 4A and 4B, 7, 8). The stop block 28 is only on one side inside the proximal actuator 20, because the opposing side is needed for the hypoid pinion 49 (see FIG. 3C).

Figure 7:
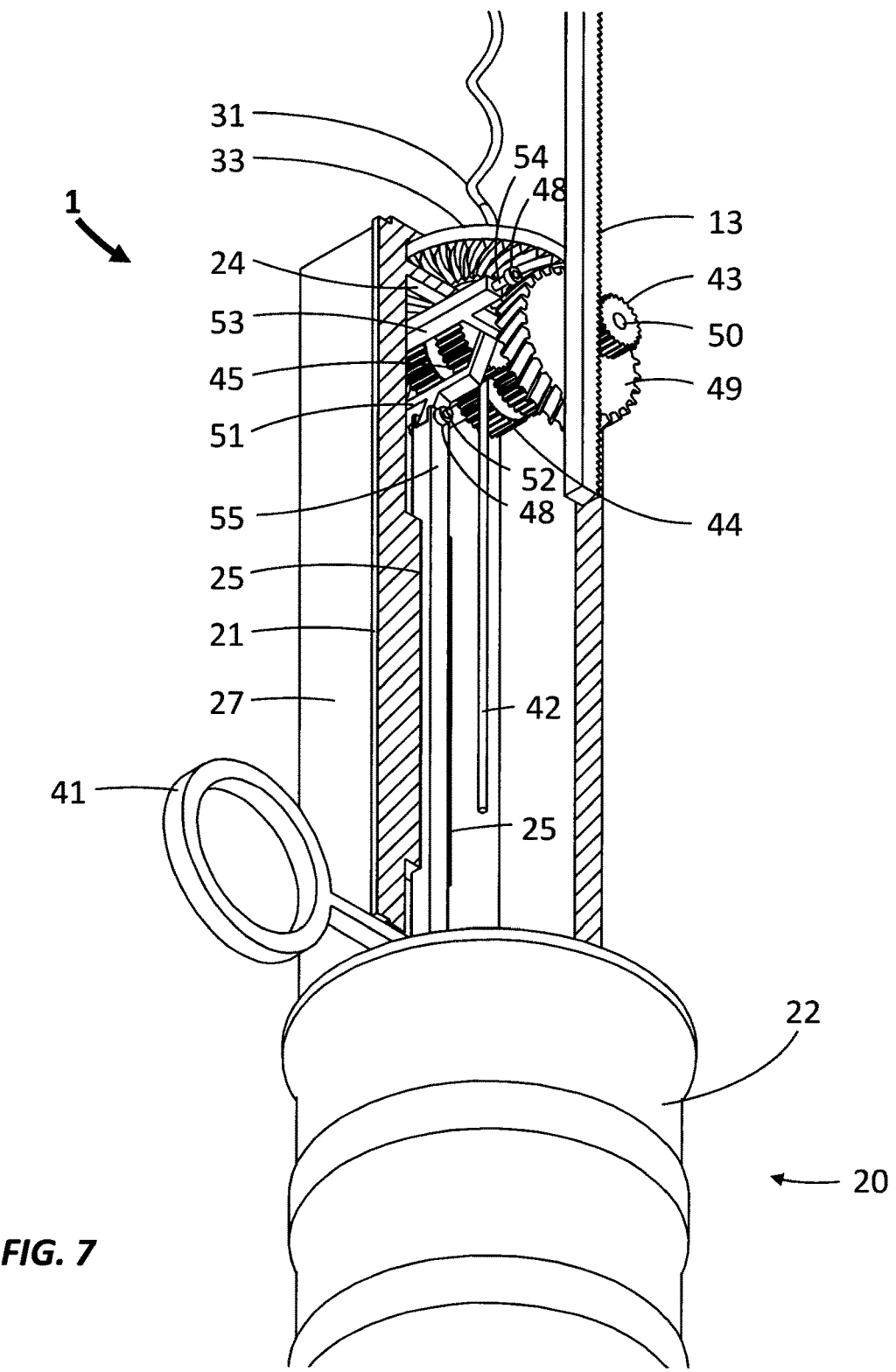
FIG. 7 is a perspective view of proximal housing with longitudinal cross section through the proximal housing in section 27 inner profile, in which only rack 13 of distal housing 10 is shown and the mechanism is in closed position.
Figure 8:
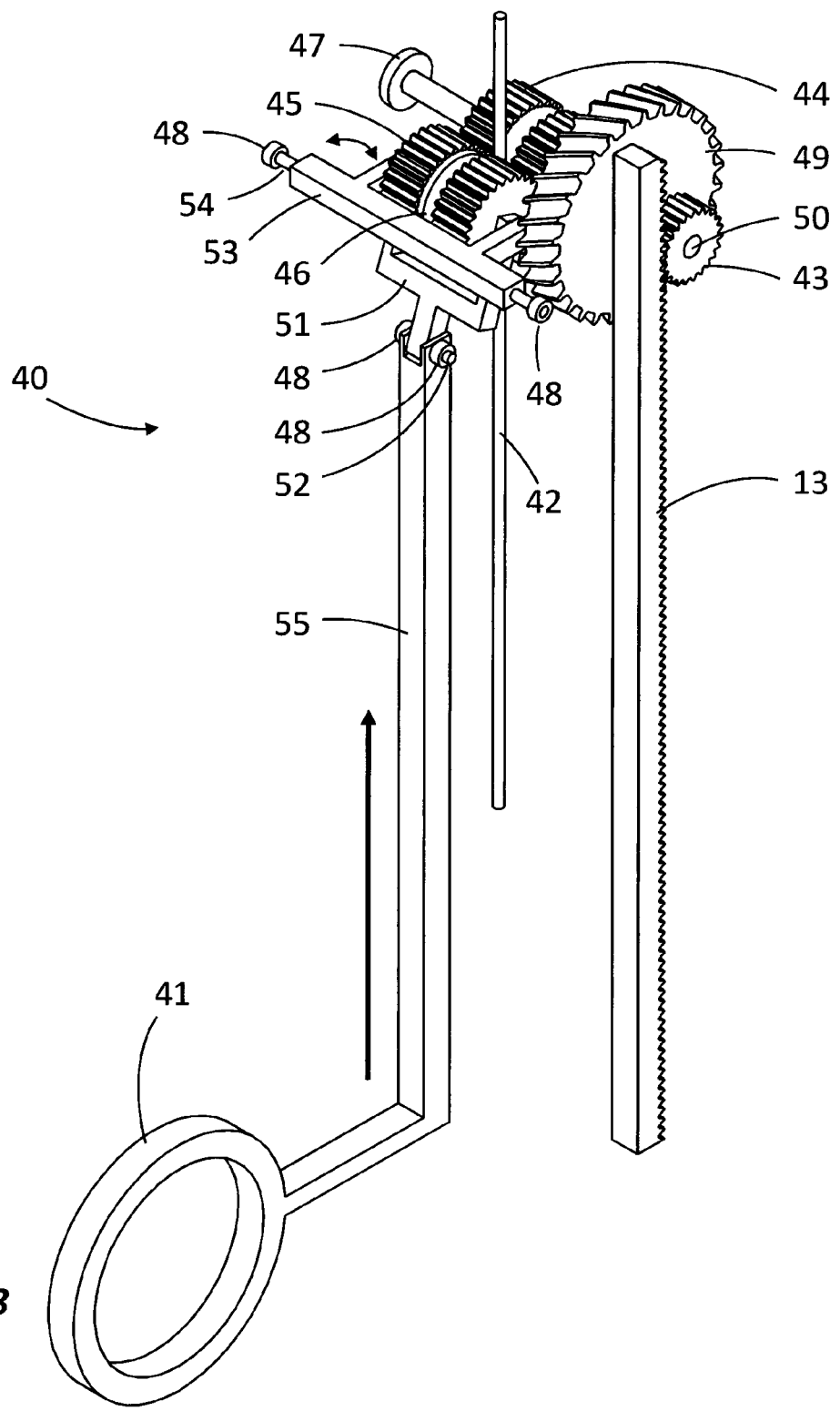
FIG. 8 is a perspective view of the drive mechanism in closed position with rack 13, not showing the housing 10.
Figures 11A, 11B:
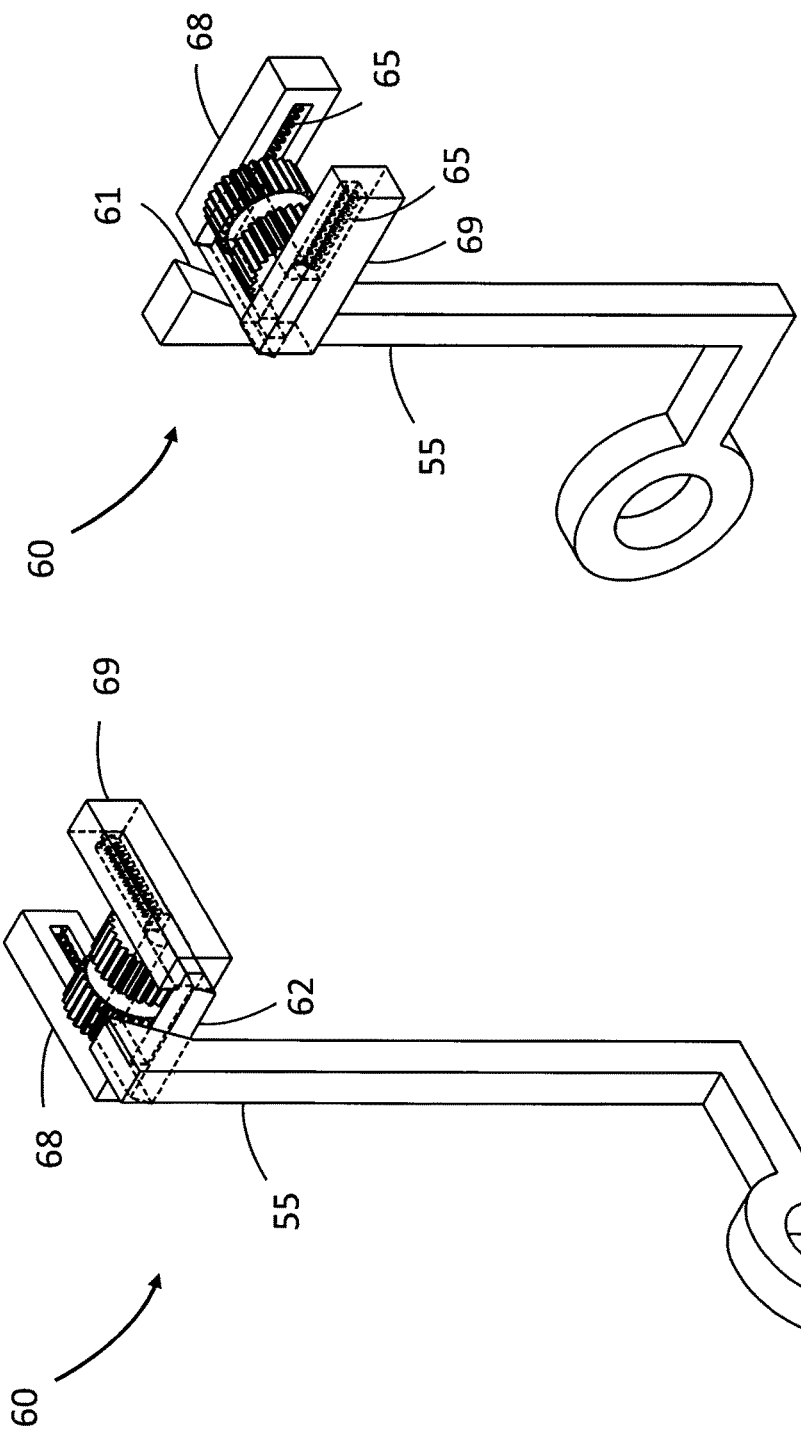
FIGS. 11A and 11B are perspective semi-transparent views showing all parts.

Referring now to FIGS. 7 and 8, the driven wheel fork 53 is manipulated through a piston engine like rod system, which translates the rotation of the fork 53 into a linear motion (fork 53 would be the equivalent of crankshaft). Accordingly, two more rods are needed in order that: the connecting rod fork 51 and the activator rod 55 (equivalent of piston); which are again connected through a fulcrum pin 52 limited by hinge pins on each side 48. The activator rod 55 slides inside the proximal housing 20 in a sliding guide 25. (FIGS. 1B, 2A, 2B, 3A-3C). The length of the rod and the position of the activator aperture 26 are designed such that, once the proximal housing 20 is fully inside the distal housing 10, the edge of the distal housing 10 pushes the rod 55 down automatically and activates the mechanism. The rod 55 must remain in that position for the entire withdrawal of the proximal housing 20 out of the distal housing 10, until the needle is at least about 1 cm outside the tissue. In an exemplary assembly, the forefinger keeps the trigger 41 in that position and helps in withdrawing the proximal actuator 20 as well. Alternatively, a latch mechanism could achieve the same result (not shown in the drawings).

Referring to FIGS. 9-12, an alternative wedge triggering mechanism 60 operates upon being pulled as well. In this embodiment, a sliding wedge 61 of the rod 55 pushes the corresponding wedge 62 of a sliding axle part 63 forward inside a spring 65 biased shaft 68 and 69 of the proximal actuator housing 20. The angle of the wedge determines forces vs. distance as indicated in FIGS. 12A and 12B. The index finger can easily pull/push the trigger 41 over a distance of 10 mm Because the driven wheel 45 needs to be dislocated only by a short distance (2-5 mm), the wedge angle can be smaller than 45° (in the drawings it is) 20°). Pulling the rod 55 pushes the sliding bar 64 of the axel part 63 along a sliding guide 67 of the shaft on the left 68 and right 69. The driven wheel 45 on the axle 66 is therefore not rotated about the fulcrum, the linear pulling force of the rod 55 is transformed into a linear pushing motion for the axle part 63, which makes it possible for the groove of the wheel 46 to be even closer to the proximal needle aperture 39. Without a latch for the rod 55, letting go of the trigger 41 with the index finger will disengage the mechanism. As the surfaces of the wedge 61 and 62 are made so as to be of low friction, the spring 65 inside each shaft 68 and 69 will push the sliding axle part 63 towards the rod 55, moving it to an initial position.

Insertion Wheels

For the insertion wheels 44/45, three things have to be considered: (1). a groove changes the diameter of the wheel, in which the member 42 is in contact, resulting in change of circumference; (2). the member should not be bruised, which is determined by force distribution (groove and/or materials); (3). The outer hull of the member 42 is most probably a fluoropolymer, essentially all varieties of which have extremely low frictional properties which effects the grip between member/wheels.

Referring again to FIGS. 7 and 8, in an exemplary assembly, both wheels 44 and 45 are grooved and of the same diameter as lateral gearings, which is the preferred solution. Whether a groove having a changing wheel diameter influences the correct distance of the member to be pushed out, is a question of relative sizes between the diameter of the wheels and the diameter of the member they push. If the wheels are, for example, only 5 mm in diameter, and the diameter of the member is 1 mm, a half groove would decrease the diameter by 0.5 mm, which equals a decrease of 10% and leads to a reduction of circumference of 1.6 mm (15.7-14.1) per turn which needs to be considered in order that the mechanism guarantees that for each unit of distance the needle retracts, the member will be pushed out by the same distance. The problem can be avoided by increasing the diameter of the wheels 44/45.

The groove 46 allows for equal force distribution over a larger contact area between wheels and flexible member 42, as well as maintaining the member 42 inside a confined space for free rotation when the fork 53 is open by creating a tiny gap between the grooves during the inserting procedure. The gearing is cut in a manner so as to adjust for decreased diameter of the groove as well as to transmit forces between the wheels without slipping.

However, there exist other possibilities to achieve the same result. The groove 46 may have a tiny band of rubber disposed about it to further avoid bruising of the member 42 as well as decrease the possibility for slippage. More aggressive gearings or knurlings can thus be avoided except where the wheels are made of hard material with low friction values (metal, hard plastic) that do not create enough friction to generate the required force transmission. In fact, the wheels do not needs grooves where the wheels are made of a soft material (rubber or the like), so that the wheels may be placed in contact to the member and/or against each other to generate friction. If the drive wheel is half-grooved and made of hard material, then the driven wheel could be un-grooved and without gearing, provided it is made of a soft material. The driven wheel turns just by pressing the implantable member into the groove of the drive wheel 44. These are only general design constraints, since the actual design of the groove and materials of the wheels largely depend upon the specific characteristics of the member 42 regarding required force and force distribution for pushing.

Rotation Directions of Gears

Rotation directions seen as in perspective view FIG. 7 of an exemplary assembly; CW—clock wise; CCW—counter clock wise Whether the helix of the needle is right handed or left handed determines rotation directions and gear design. The helix orientation given, there are two setups that achieve this result: to rotate the needle in the required direction and to push out the member when withdrawing the actuator. Position/side of rack 13 vs. pinion 43 determines the shaft 50 direction and with that the position for the hypoid pinion 49.

Left-handed helix needle: to screw in, the needle part 30 must rotate CCW. The position of rack 13 (left) and pinion 43 (right) makes the shaft 50 turn CCW when pushing inside. As a result, the hypoid gear pinion 49 must be on the main drive pinion 43 side of the shaft 50 for making the needle part 30 turn CCW. When withdrawing the inserter, the shaft 50 will turn CW and serve as an axle for the drive wheel 44 to push the member into the needle aperture 39.

Alternatively, the contact side of rack 13 and pinion 43 may be switched, with the shaft 50 turning CW when pushing in, the hypoid pinion 49 switched to other side of pinion 43; and switching the side (right of shaft) of the driven wheel 45, but this is considered geometrically undesireable.

Right-handed helix needle: vice versaGear matching: Calculating the adequate gear transmission:

Because the wheels push out the member, the bigger the diameter means greater contact area, and so no bruising of the member. However, the contact area depends on the fragility of the member. As the wheels are to insert a highly complex, filigree and fragile member, the diameter of the wheels 44/45 is chosen to be 10 mm in this example; the other values are already determined by the needle.

Given:

$D$=Diameter of helix=arc length×2

P=Pitch
N=Number of turns of helix
W=Diameter of member injection wheels
H=Height of helix Find:
$L_T$=Total length of helix
A=Diameter main drive pinion 45
$gr_{hypoid}$=Gear ratio hypoid drive
F=Diameter of hypoid pinion 49
G=Diameter of needle drive crown wheel 33/34

Total Length of Helix:

The circumference of a circle of diameter D is: $C=\pi \times D$

Now if we stretch this circumference, it will form the base of a triangle whose other leg is equal to the pitch of the helix. Hence the length of the wire that makes one helix turn is the hypotenuse of the triangle which is:

$$L_C = \sqrt[2]{C^2 + P^2}$$

The total length of the helix therefore is:

$$L_T = N \times L_C$$

Diameter A of Main Drive Pinion 45:

The wheels need to push out the length of the helix over the pull back distance $$\text{No. turns required drive pinion } T_{req} = \frac{\text{Total lenght of helix } L_T}{\text{circumference drive wheel}}$$

$$= \frac{L_T}{W \times \pi}$$

$T_{req}$ is the no. turns the pinion needs to make over the pull back distance $$\text{Circumference drive pinion } A \times \pi = \frac{\text{Height of helix } H}{\text{No. turns required drive pinion } T_{req}}$$

$$= \frac{H}{T_{req}}$$

Filling in and Solving for Diameter of the Pinion A:

$$A = \left( \frac{H}{N \times \sqrt[2]{(\pi \times D)^2 + P^2}} \right) / \pi$$

$$\phantom{A = }\frac{}{W \times \pi}$$

Gear Transmission Ratio for the Hypoid Drive $Gr_{hypoid}$:

$$gr_{hypoid} = \frac{\text{circumference drive wheel} \times \text{No. Helix turns}}{\text{Total lenght of helix } L_T}$$

$$= \frac{W \times \pi \times N}{L_C \times N}$$

$$= \frac{W \times \pi}{\sqrt[2]{C^2 + P^2}}$$

$$gr_{hypoid} = \frac{W \times \pi}{\sqrt[2]{(\pi \times D)^2 + P^2}}$$

The above yields the ratio that the hypoid drive must provide. Once one diameter of one wheel is chosen, it can be solved for the other.

Materials, Sizes

By choosing the diameters of the gears well, hard plastics may be used. The needle is preferably medical grade metal. Even the bearings may be made of solid plastic so as to exhibit dry-running lubrication-free behavior.

General Design Constraint for Screw Thread Inserter

Referring now to FIGS. 13a to 17b, an alternate embodiment uses a screw thread 110 to drive the inserter and includes a distal housing 100 with a female left hand screw thread 110 inside, a left-handed helical hollow needle 210 affixed to a screw thread drive wheel 220, which is freely rotatable coupled to the proximal actuator housing 300. As the actuator 300 is pushed into the distal housing 100, male pins or cam follows 230 (best shown in FIGS. 27a and 27b), engage the threads, which in combination with the female thread 110, force the wheel 220 to screw inside the distal housing 100, which forces the helical hollow needle 210 to pierce the tissue along a helical path. Screw thread orientation and pitch of distal housing and helical hollow needle must be equal so that the pierced tissue isn't expanded or contracted. A suitable relationship between helix needle arc length, height, turns and the inner diameter of the screw thread housing 100 must be determined to ensure proper operation. Referring in particular to FIG. 42, a layout compares the screw thread helix of distal inserter and corresponding pitch angle with the helix of hollow needle and corresponding pitch angle. The path A represents the screw thread helix of the distal inserter and corresponding pitch angle, wherein the helix specs are the same, but the arc length is doubled to 6 mm, resulting in a pitch angle of 31 degrees. The path B represents the helix of the hollow needle and corresponding pitch angle, where the arc length is 3 mm, the height 76 mm, the number of turns is 4, which results in a pitch angle of about 48 degrees The inserter only works if the pitch angle (helix angle) of the screw thread inside the distal inserter is large enough. The smaller the angle, the more of a wedge effect it creates. The largest possible angle (theoretically) is restricted by the diameter of helical needle which must fit through the distal inserter (indicated by dashed lines). Since the screw thread is on the inner side of the distal housing, this diameter must be larger than the one from the hollow needle. Larger diameter means smaller pitch angle. Therefore the helix of the hollow needle influences the size (diameter) of the entire inserter. As mentioned, the pitch angle of an exemplary needle is only about 48°, with a diameter of 6 mm. As a result, the entire member push out mechanism must fit inside it. In order to generate more space, the diameter of the distal inserter could be increased, which increases the diameter of the helix screw thread as well. However, at a certain diameter, the pitch angle of the screw thread drops below 30° and the wedge effect starts to set in. In the example, if the inner diameter of the distal housing is 12 mm, the resulting pitch angle is already about 31°. Therefore, there is give and take with this embodiment. This embodiment uses components with very low friction forces between the inner surface of the distal housing 100 with screw thread 110 and the wheel 220 of the needle with its pins 230 gliding along.

In more detail, in this embodiment, the distal housing 100 is either held with one hand or mounted on a rack using the fixation arms 160. Once the distal housing 100 is orientated regarding tissue access point and axis, the proximal actuator housing 300 is pushed inside as indicated by the arrow in FIG. 13*a*. This screws the needle 210 helically inside the tissue. When the actuator 300 is fully inside the distal housing 100, the push-button 360 is pressed, which activates the drive mechanism inside 300 through a control rod 350. Now the actuator 300 is pulled out of the distal housing 100 and the implantable part 500 is automatically pushed out of the needle 210. Once the actuator reaches the end of the distal housing 100 and the needle 210 is outside, the push-button 360 is pulled back or released into its initial position in order to disengage the drive mechanism. Now the implantable member 500 can be held by hand or some sort of clamp at the distal needle tip side 215 to cautiously pull the remainder of the implantable part 500 through the inserter and out of the needle 210. This completes the process of inserting the member.

The outer surface of the screw thread drive wheel 220 and inner surface of the distal housing 100 should be nearly form fitting (i.e., exhibit very little play) and the cylindrical wheel 220 should be of sufficient height, that the two parts cannot jam or seize. As indicated in FIGS. 24, 25, 29, the proximal actuator housing 300 is of lesser diameter than the screw thread drive wheel 220. However, it could be of same diameter as the screw thread drive wheel 220, except that would increase friction forces.

Figure 19:
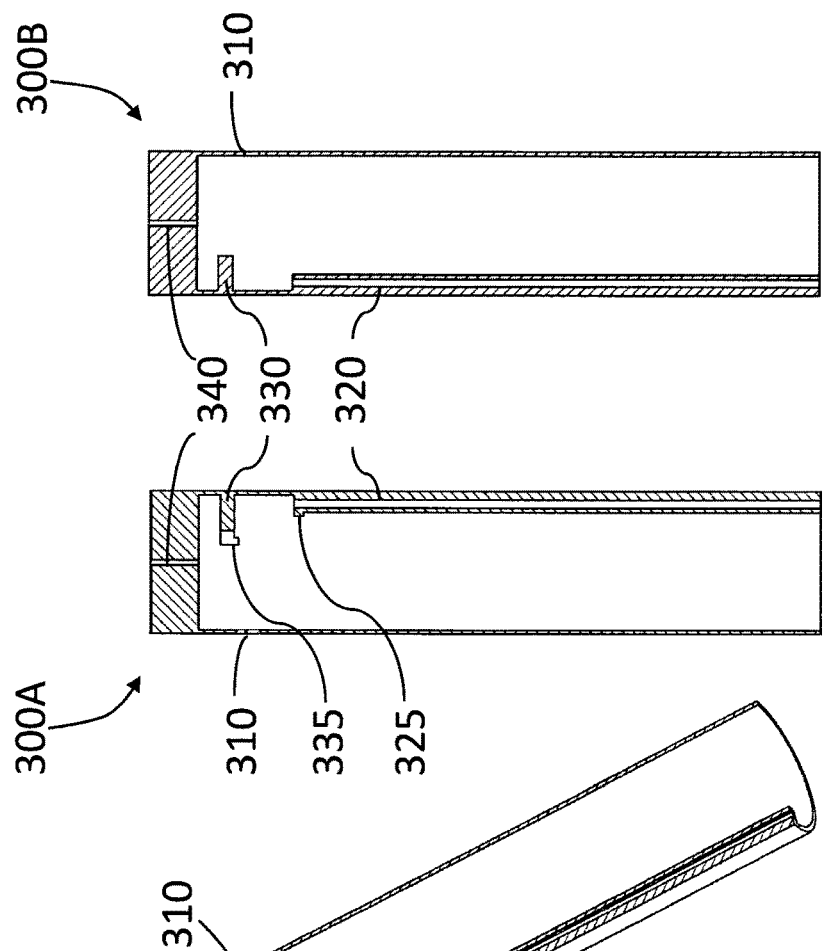
FIG. 19 shows two cross sectional views of the opposing sections of the proximal housing of the alternate embodiment of the invention.
Figure 18:
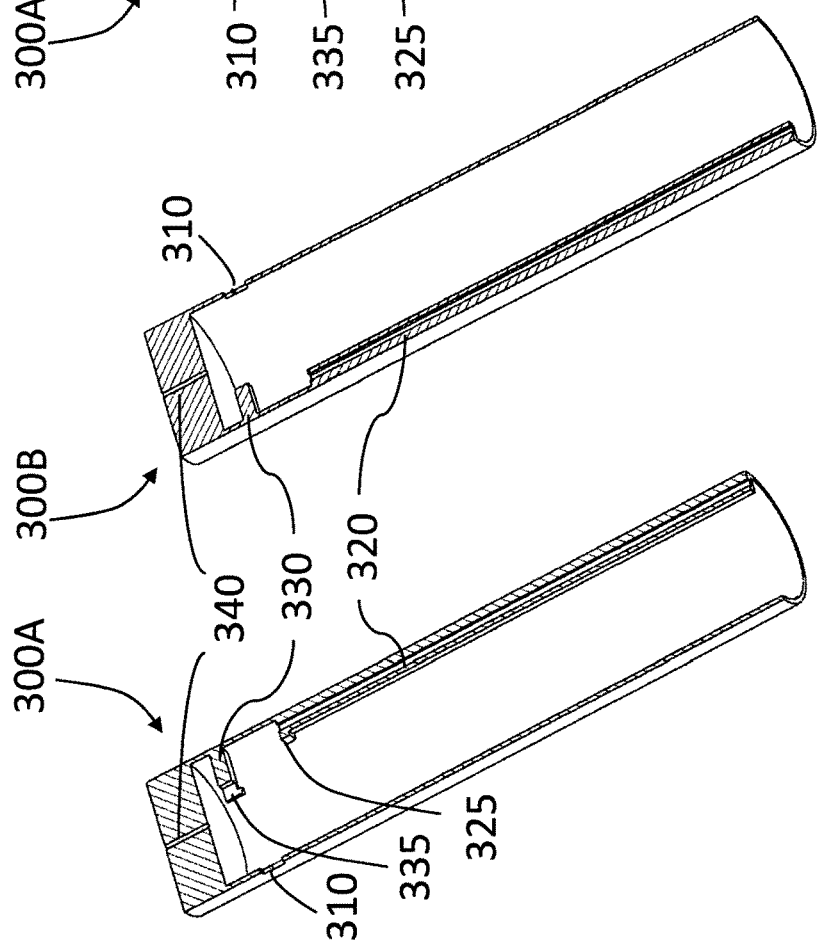
FIG. 18 shows two cross sectional, perspective views of opposing sections of the proximal housing of the alternate embodiment of the invention.
Figure 23:
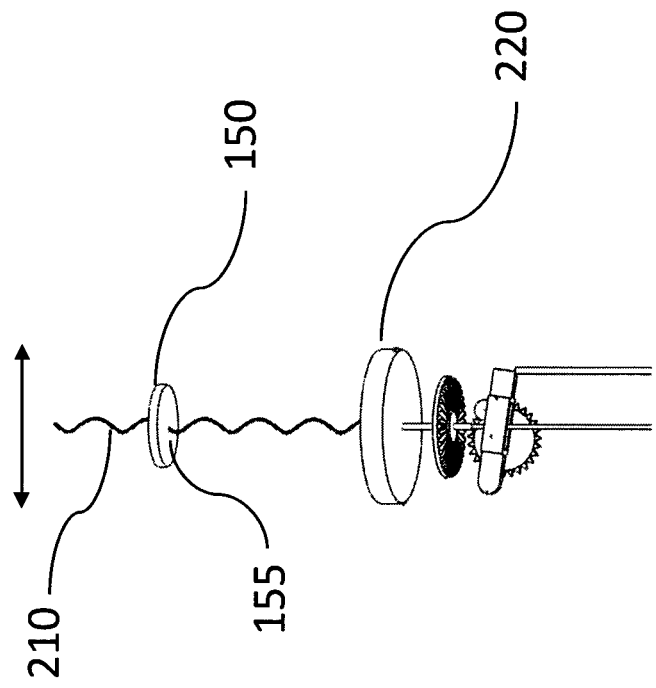
FIG. 23 is a perspective partially assembled view of the needle and gear assembly used in the alternate embodiment of the invention.
Figure 22:
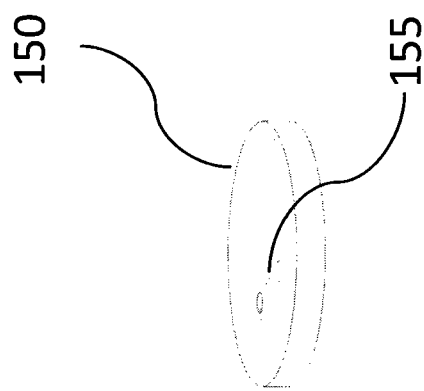
FIG. 22 is a perspective view of a part into which the helical needle mounts in the alternate embodiment of the invention.
Figure 28A:
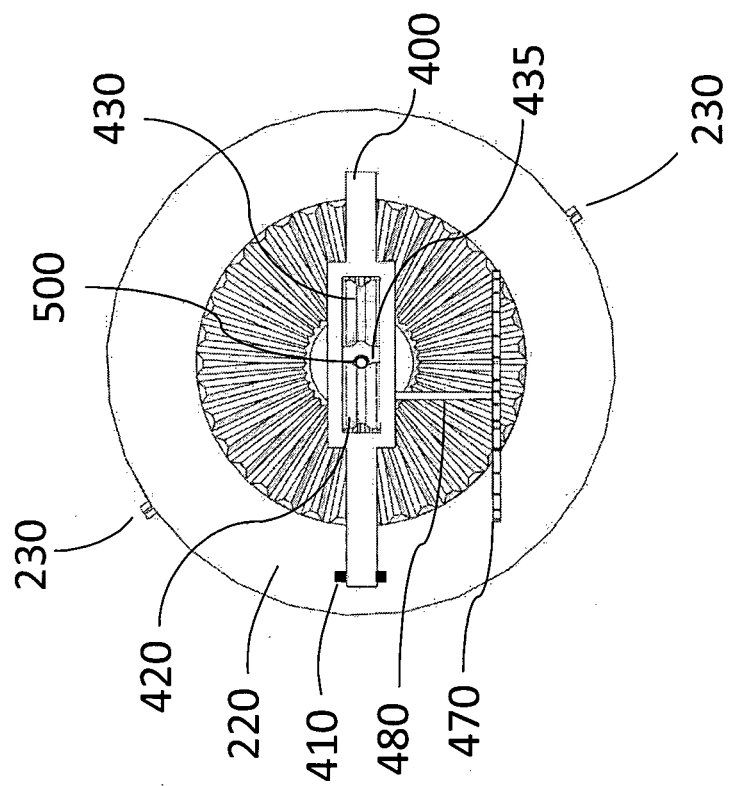
FIG. 28a is a close up, bottom, partially assembled view of the needle and gear assembly used in the alternate embodiment of the invention showing a closed position of the triggering mechanism of the invention.
Figure 28B:
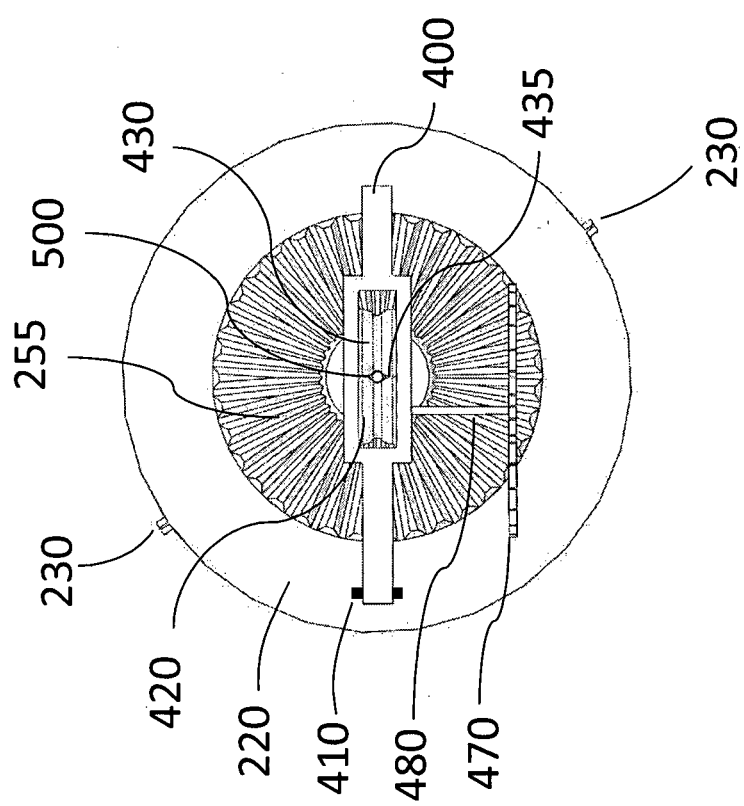
FIG. 28b is a close up, bottom, partially assembled view of the needle and gear assembly used in the alternate embodiment of the invention showing an open position of the triggering mechanism of the invention.
Figure 31:
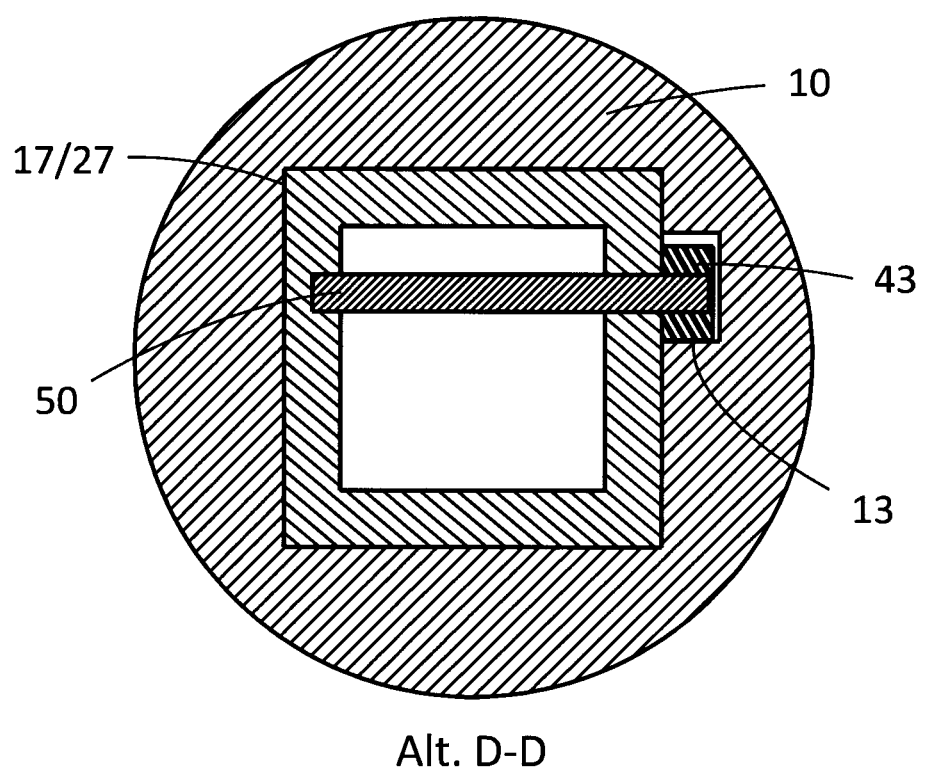
FIG. 31 is an alternate, partially assembled transverse cross sectional view D-D as indicated in FIG. 3B through the mechanism showing an other embodiment.
Figures 32A, 32B, 32C:
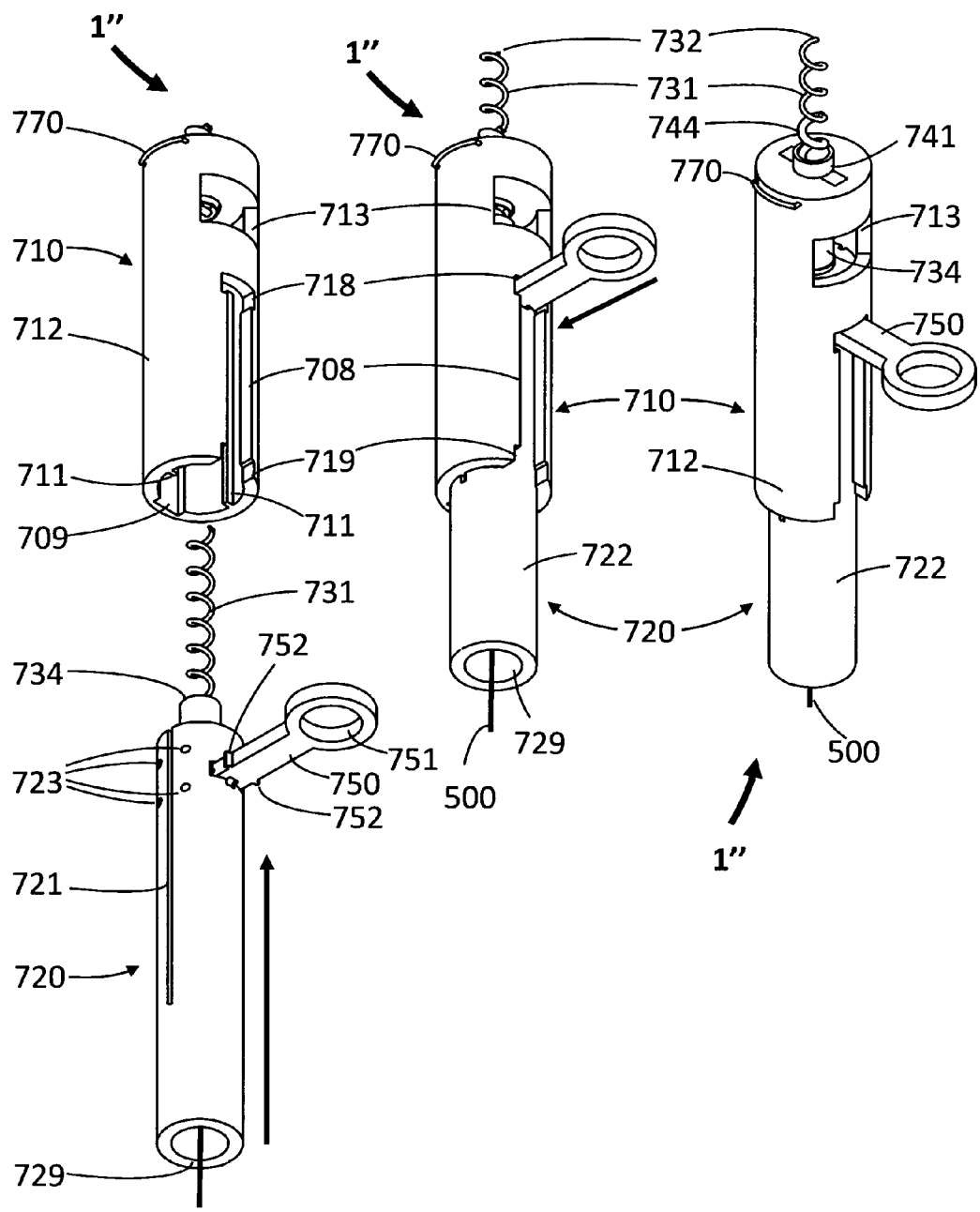
FIG. 32A is a perspective view of an exemplary injection assembly according to the present invention with distal and proximal housing separated.
FIG. 32B is a perspective view of an exemplary injection assembly according to the present invention with proximal housing inside distal housing (fully injected).
FIG. 32C is a perspective view of an exemplary injection assembly according to the present invention with proximal housing inside distal housing (fully injected).

The male screw threads or cam followers, indicated as pins 230, are not limited to only one or two; optionally multiple threads could be used. For the thread form of the female thread 110 and pins 230, there are numerous different profiles in use today. Small play of the screw thread drive wheel 220 and distal housing 100, height of cylindrical screw thread wheel 220 and the threadform 110 and 210 can be selected to guarantee that the needle part 200 screws into the distal housing 100 with low friction forces and no possibility to cant and jam. The needle 210 with the drive wheel 220 must be freely rotatably coupled to the proximal actuator housing 300. Referring now to FIGS. 18 and 19, the axle bushing 340 through the center of actuator 300 provides a bearing surface for the hollow driving shaft 240. The inside and outside of the housing 300 together with wheel 220 and 250 restrict movement in the perpendicular plane. Again, friction forces should be low by choosing adequate materials.

In the drive inserter of FIGS. 1A-8, the rack 13 and pinion 43 must drive the needle 30 and the push out mechanism through a shared shaft 50. In contrast with the drive inserter solution, the screw thread drives the needle directly—only force transmission for the push out mechanism is needed. The mechanism needs to fulfill the same function: it must be disengaged while inserting the needle with the member being free to rotate, and engaged when withdrawing the needle until it is outside the tissue, to disengage it again and pull the remainder of the member through the needle.

Referring now to FIGS. 24A-30, a drive and a driven wheel again needs to push the flexible member or insert 500 inside the proximal aperture 245 of the needle. The rotating force of the mechanism drive wheel 250 needs to be translated to a push out force for the member. The direction of the drive carried by the hollow shaft 240 has to be transferred through 90 degrees to drive an axel 480 with a drive wheel 420 affixed on it. Again, the aperture 245 lies in the center of the axis and so a bevel gear solution is not feasible without more parts. Therefore, the axle 480 needs to be offset again, which results in a hypoid gear design, as can be seen in FIGS. 27*a* and 27*b*. Because of the small forces required to push out the member, the hypoid gear can be a straight cut gear 470. Hypoid gears can be made with straight-cut gears, if applied forces are low, as in this application. In the drive inserter solution, the forces applied on the gearing are higher because it must produce the force for the needle to rotate and pierce the tissue. Here, the hypoid gearing produces the force needed to push the member into the aperture of the needle, which is substantially lower. In contrast with the drive inserter, this approach disconnects the member push out mechanism completely, which means that the drive wheel 420 is not turned during the needle inserting procedure, If only the driven wheel 430 should be disconnected, the two mechanisms described in FIGS. 1-12 work as well. A bridge element 400 turning about a fulcrum pin 410 inside the groove 310 of the housing 300 serves as a second class lever and dislocates the straight cut hypoid gear 470 from the drive gears 255 of the mechanism drive wheel 250. By pressing the push-button 360, the control rod 350 inside a sliding guide 320 forces the bridge to rotate about the fulcrum 410/310 inside the housing. The hypoid gear 470 is connected through driving shaft 480 with the drive wheel 420 inside the bridge. The driven wheel 430 is mounted on a first class lever, turning about a fulcrum pin 460 connected to the bridge 400. One side of the control lever 440 serves as fixation arm for the axle 465 of the driven wheel 460. The other side of the control lever 450 is spring loaded 490/495. With the lever in parallel position to the bridge, the driven wheel 430 is in contact with the drive wheel 420, which is referred as the closed position or mechanism engaged. In initial (disengaged) position, the spring pulls the control lever 450 towards the spring fixation 325, which in turn pulls the bridge 400 with it. Pushing the button 360 activates the drive mechanism, as indicated in FIG. 24.

Referring now to FIG. 18, 19, 29, the control rod 350 pushes the bridge 400 towards the positive stop block for the bridge 330 and the hypoid drive is in contact with the drive gears 255. By pressing the bridge upwardly, the control lever on the wheel side 440 moves towards its positive stop block 335 as well. This pushes down the lever 440, such that the drive and driven wheel are in contact and the mechanism engaged. Pulling the button 360 will disengage the spring loaded mechanism. Regarding the drive and driven wheel design, the same constraints as with the drive inserter solution apply. The drawings for the screw thread inserter show a solution without gearings. Now referring to FIGS. 41A and B, in another embodiment 1''', a needle locking mechanism in combination with the mechanism of the rod 350 and the bridge 400 already described, allows for screwing, rather than pushing, of the proximal inserter housing into the distal housing by means of locking the mechanism drive wheel 250 with an arm of an prolonged rod 350. When screwing the proximal housing in, the locking arm 351 blocks the needle through the groove 260 in wheel 250. Once screwed in, activating the mechanism of the bridge through 352 also unlocks the wheel 250. The proximal inserter housing must of course have a corresponding groove for the now longer rod 350. Pulling the proximal housing out of the distal works now as previously explained. To activate, the button 360 is first pushed in one direction for the arm 354 to move inside the proximal housing by means of bending. Once the arm 354 clears the housing, the button can be pushed inside as already described, further integrating a groove 355 to lock the arm 354 to hold the rod and therewith the bridge in active state.

Referring now to FIGS. 16a, 17a, 22 and 23 which deal with the stability of needle: The needle could be provided with further stabilization before exiting the inserter and then entering the soft tissue. Stability can be provided by several means. Two exemplary possibilities include a conical aperture and a special, needle stabilizing aperture.

Referring now to FIGS. 16b to 17b, item 130, if not 5a, aperture 130 through distal housing 100 may be slightly conical, with diameter of helix of the needle (the outer diameter) so that the needle always fits inside the conical aperture 130 at the proximal side, as distal and proximal handles 100, 300, respectively, are assembled. The distal aperture side is of equal diameter to the needle 210. This stabilizes the needle.

Alternatively, a needle stability aperture stabilizes the needle. A disk holder 140 is provided inside distal housing 100 for the stability aperture disc 150, which has an aperture 155 for the needle 210 to run through. This is similar to U.S. patent Ser. No. 11/834,186, to Rioux, mentioned in the background, except that there is no guide aperture because it doesn't "guide" the needle in terms of rotation forces, pitch, no. turns. Rather, it rotates freely and therefore it can only add to the stability of the needle before being pushed into the tissue in the transversal plane as indicated with the arrow in FIG. 23.

Referring now to FIGS. 32-38, an alternate embodiment uses a helical guide tube 740 to make the needle 730 turn and move along its helical pathway and a push out mechanism for the member 500 without a rack and pinion or a drive mechanism as already explained, rather using only wheels with a rubber surface. Unlike the inserter embodiments already explained, here the mechanism for the needle and the push in mechanism are separated from each other with no direct force transmission between these two. As shown in FIG. 40, it should be noted, as already explained with the other inserter types, that the implantable flexible member 500 may already be inside the needle 731 just before the tip 732 before the beginning of the inserting procedure, and so passes all the way through the hollow needle and out of the proximal needle aperture 733. The member is flexible having an inner 501 structure and a low friction outer hull 500, for example a fluoropolymer which are corrosion resistant and biocompatible, in contact with the inner wall of the needle 731. The outer hull of the member 500 and the inner wall of the needle 731 is separated by a small gap 502, which could be filled before insertion with an antiseptic fluid or lubricant.

This type of inserter is of particular benefit if only a soft tissue structure posterior to another structure of the body should be pierced helically, leaving the structures superficially intact. Referring now to FIGS. 36, 37A and 37B, the guide tube 740 can be separated from the distal inserter housing 710 for ease of handling and placing at the site that should be pierced helically without having to move the rest of the inserter with it. A small incision is necessary to access the site, and the helical guide tube 740 held between thumb and fingers is cautiously slipped in until the distal guide orifice 745 reaches the desired location from which helical piercing should begin, for example, between or under muscles. The distal orifice 745 is of rounded shape having no edges which might damage the tissue. Only placing the orifice 745 of a helical tube on site where the helical piercing should start can guarantee that superficial structures are unharmed by the helical needle 730 and superficial tissue layers unstreched. The helical guide tube 744 should have the same pitch and diameter of the helix as the needle 731 which is pushed through it (or withdrawn from it) and which is helically driven by it. The diameter of the tube 744 is slightly larger than the diameter of the needle 731 such that it slidingly fits through. Preferably the helical guide tube 744 and the helical needle 731 are made of medical grade metal which could cold worked and formed using a CNC-controlled coiling and bending machine for the production of torsion springs or tension springs, for example like the FMU series from producer Wafios of Germany. The helical tube 744 is affixed to an over tube 741, for example by means of laser spot welding, to create a simple form for docking the helical guide tube 740 to the distal housing 710. Furthermore the tube 741 might be cone shaped on the proximal end 742 to fit easily into the needle guide port 715 of the distal housing 710. With the guide tube 740 held by fingers in its position and the distal orifice 745 being inside the body at the desired location, the distal housing 710 is moved towards the guide tube 740 to first dock with and then lock both. For the fixation of the guide tube 740 to the housing 710, arms 743 are mounted to the tube 741. The arms 743 are wedge shaped to fit easily into the corresponding groove of the distal housing 710 when docking the guide aperture 740 through the needle guide port 715 to the distal housing 710.

A suitable locking mechanism is provided for locking the helical guide tube 740 to the distal housing 710. Referring now to FIGS. 32, 33, 36 and 37, the helical guide tube 740 is locked to the distal housing 710 by means of a fork like pin fastening mechanism 770 that can pressed into holes 717 of the distal inserter 710, preferably in a manner to snap in place. The holes 717 pass through the docking port 715 and into holes 747 in the arms 743 of the guide tube. The arms 743 have corresponding holes 747 along the axis of the inserter holes 717. With the guide tube 740 docked to the port 715, pushing the fork pin 770 into place locks the guide tube 740 to the housing 710.

Referring now to FIG. 39A, in an alternate embodiment, the helical guide tube 740 is locked to the distal housing 710 by means of a bayonet fastening mechanism 760. The distal housing provides a bayonet slot 716 for the bayonet pins 762 of the bayonet 760. Referring now to FIGS. 39B and 39C, turning the bayonet 760 changes the position of the arm clearance slot 761. FIG. 39B shows open state, the arms 743 of the guide tube 740 can now be docked into the port 715. FIG. 39C shows closed position: turning the bayonet 760, as indicated with the arrow, locks the guide tube 740 to the distal housing 710 as the arm clearance slot 761 is now blocking the arms 743.

Now referring to FIGS. 32A to 32C and 33A to 33C, with the helical tube 740 locked to the distal housing 710, the trajectory of the inserter must be assured as already explained. Next, the proximal actuator housing 720 can be inserted into the distal housing 710 using the corresponding sliding guide 711 and 721.

The needle part 730 must have a sliding contact bearing with the proximal housing 720. For that, two discs 738 and 739 (see FIG. 38) with a hole in center are affixed to the tube section 736 of the already formed needle. The sliding contact disc 738 serves only as a bearing surface together with the corresponding profile inside the proximal inserter 720. The second disc 739 serves to distribute forces: once affixed to the needle, it is used as a base for the tube 734. The tube 734 is affixed to the helix section 737 inside the tube as well as to the disc 739 to better distribute the linear force exerted by the pushing in of the proximal inserter 720. In this manner, a simple supporting structure can be created for the structurally weak section 736, 735 to the helix section 737, which allows keeping the wall thickness of the needle to a minimum.

Now pushing the proximal housing 720 inside the distal 710, as the tip of the needle 732 reaches to proximal guide orifice 746, the needle part 730, which is freely rotatably coupled to the proximal actuator housing 720, must be put inside the proximal orifice 746 by putting thumb and index finger through the window 713 of the distal housing 710, holding the needle 731 just below the tip 732 and placing it into the cone shaped proximal orifice 746. For this reason, the proximal tube orifice must be outside of the tube 741, and the tube itself must be long enough to fit through the whole profile of the distal inserter housing 710 at the needle guide port 715. From now on, while pushing the proximal housing 720 into the distal housing 710, the helical guide tube 740 forces the needle 730 to rotate along its corresponding helical pathway, as can be seen in the transparent view of FIG. 38. As the needle tip 732 reaches the distal orifice 745, the helical piercing of the soft tissue begins along the central axis of the distal housing 710. Once the proximal housing 720 is fully inside the distal housing 710, the needle 731 is also fully inside the tissue along its helically pierced pathway. In this embodiment, the trigger 750 acts as a positive stop block, but, of course, other solutions are possible, and may, for example, include a stop block inside the distal housing 710. A stop block avoids contact between the tube 734 of the needle 730 and the proximal orifice 746 of the guide tube 740, as it might otherwise bend or damage these parts.

Figures 33A, 33B, 33C:
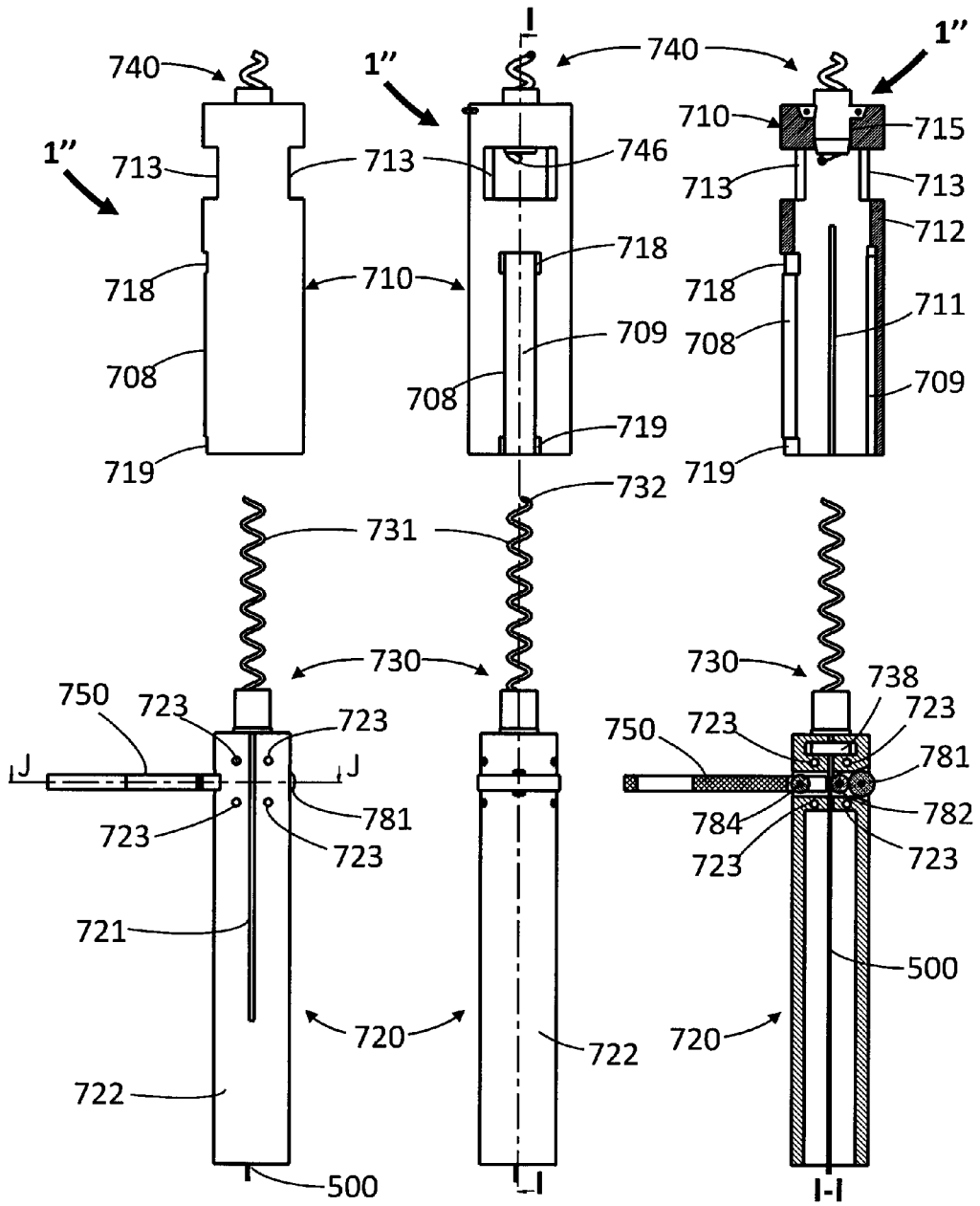
FIG. 33A is a front view of an exemplary injection assembly.
FIG. 33B is a side view of an exemplary injection assembly.
FIG. 33C is a longitudinal cross sectional view I-I as indicated in FIG. 33B through distal and proximal housing, mechanism inside excluded from cross section, member push out mechanism open (deactivated), like during inserting procedure of needle into tissue.

Now referring to FIGS. 34A to 34D, which is a cross section I-I as shown in FIG. 33B and the corresponding transverse cross section J-J as in FIG. 33A, showing the proximal inserter inside the distal housing 710 at four different states. FIGS. 35A and B are transverse cross sections J-J, side by side layout showing the trigger 770 in two extreme positions of FIG. 34A and FIG. 34C.

FIG. 34A shows the proximal inserter fully inside the distal housing 710, the trigger 770 acting as a stop block. The wings 752 of the trigger are outside the distal housing 710 and the member push out wheels 782 not in contact, leaving a gap open.

FIG. 34B shows the proximal inserter fully within the distal housing 710, the trigger 770 being pushed inside through the activation trigger aperture 718 for the wings 752. The member push out wheels 782 are now in contact with the member 500 disposed between them. The drive wheel 781, in contact with the back wall 709 of the distal inserter, can now drive the whole mechanism.

FIG. 34C shows the proximal inserter 720 half way outside the distal housing 710, the needle tip 732 being already inside the guide tube orifice 745, showing the member 500 as it would be inside the tissue. The wings 752 are confined in its groove inside the proximal inserter 720 by the inner wall of the distal inserter 710 keeping the wheels 782 closed and the mechanism active.

FIG. 34D shows the proximal inserter 720 just before leaving the distal housing 710. The trigger 770 can now be pulled out, disengaging the mechanism and leaving a gap for the member 500. The tip of the needle 732 is already outside the proximal needle orifice 732 and the member 500 can be grabbed by fingers through the window 713. The length of the member 500 on the proximal side of the inserting wheels must at least the length inside the needle; otherwise the member cannot be fully inserted. The inside diameter of the guide tube 744 is substantially larger than the inside diameter of the needle 733, allowing the member 500 to be pulled easily through the guide tube 740.

In an advantage of the invention, the invention provides a method and apparatus for inserting an implantable member helically into soft tissue, thereby better fixing the implantable member through the structure of the helical pathway in the soft tissue when such tissue is deformed.

In another advantage of the invention, an improved electrode is provided for insertion into deformable body sections, especially muscle tissue which undergo a change in length between septum access and distal location of the member.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification, inclusive of the appendix hereto and any computer program comprised therein.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

APPENDIX

| Element list |  |
| --- | --- |
| Helical Needle Drive Inserter 1, reference lists: | |
| 10 | Distal inserter housing |
| 11 | Sliding guide |
| 12 | Distal handhold |
| 13 | Rack |
| 14 | Needle orifice port |
| 15 | Skin tension boss |

APPENDIX-continued

Element list

| | |
|---|---|
| 17 | Inner profile of distal inserter, corresponding 27 |
| 20 | Proximal actuator housing |
| 21 | Sliding guide bars |
| 22 | Proximal handhold |
| 23 | Proximal actuator top, top sliding contact bearing for needle drive wheel |
| 24 | Needle bushing beam, bottom bushing for needle tube section 36 |
| 25 | Sliding guide for activator rod |
| 26 | Aperture for activator rod |
| 27 | Distal profile of proximal inserter |
| 28 | Stop block for 53 |
| 29 | Aperture for member 42 |
| 30 | Needle part |
| 31 | Helical hollow needle, right-handed |
| 32 | Helical hollow needle centrically bending section |
| 33 | Needle drive crown wheel |
| 34 | Hypoid gearing |
| 35 | Elevated sliding contact |
| 36 | Hollow needle tube section |
| 37 | Needle tip, distal hollow needle aperture |
| 39 | Proximal needle aperture |
| 40 | Inserter mechanism |
| 41 | Inserting mechanism activator trigger |
| 42 | Implantable member |
| 43 | Main drive pinion |
| 44 | Member injection drive wheel, geared laterally |
| 45 | Member injection driven wheel, geared laterally |
| 46 | Half-round wheel groove, 2 × groove width = diameter member 42 |
| 47 | Shaft hinge pin |
| 48 | Hinge pin |
| 49 | Hypoid gear pinion |
| 50 | Shaft |
| 51 | Connecting rod fork |
| 52 | Fulcrum pin for 51 |
| 53 | Driven wheel fork |
| 54 | Fulcrum pin for 53 |
| 55 | Activator rod |

Alternate Wedge Triggering Mechanism-Reference List

| | |
|---|---|
| 60 | Wedge triggering mechanism |
| 61 | activator rod wedge |
| 62 | corresponding wedge sliding axle |
| 63 | sliding axle part |
| 64 | slide bar |
| 65 | spring |
| 66 | axle |
| 67 | sliding guide |
| 68 | shaft part (left) |
| 69 | shaft part (right); semi transparent |
| 70 | spring counter force |

Helical Needle Screw Thread Inserter 1', reference lists:

| | |
|---|---|
| 100 | Distal inserter housing |
| 110 | Female screw thread, right-handed |
| 120 | Inlet aperture for male screw thread pins |
| 130 | Conical aperture |
| 140 | Stability aperture disc holder |
| 150 | Freely rotatable stability aperture disc |
| 155 | Stability aperture |
| 160 | Fixation arms |
| 200 | Needle part |
| 210 | Helical hollow needle, right-handed |
| 210A | Helical hollow needle with proximal end bent centrically |
| 210B | Helical hollow needle with proximal end unchanged |
| 215 | Needle tip, distal hollow needle aperture |
| 220 | screw thread drive wheel |
| 225A | Straight tube through wheel |
| 225B | Helical tube through wheel |
| 230 | Male screw thread pins |
| 240 | Hollow driving shaft |
| 245 | Proximal needle aperture |

APPENDIX-continued

Element list

| | |
|---|---|
| 250 | Mechanism drive wheel |
| 255 | Drive gears |
| 260 | Mechanism drive wheel locking groove |
| 300 | Proximal actuator handle |
| 310 | Bridge fulcrum pin groove |
| 320 | Sliding guide for control rod |
| 325 | Spring fixation |
| 330 | Positive stop block for bridge 400 |
| 335 | Positive stop block for control lever 440 |
| 340 | Bushing for driving shaft 240 |
| 350 | Control rod |
| 351 | Locking arm |
| 352 | Activator arm for bridge 400 |
| 354 | Retainer |
| 355 | Locking groove |
| 360 | Push-button |
| 400 | Bridge mechnism(second class lever) |
| 410 | Bridge fulcrum pin |
| 420 | Half-Round groove member injection drive wheel |
| 430 | Half-Round groove member injection driven wheel |
| 435 | Force transmission edge between 420/230; optionally geared surface, gear ratio 1:1 |
| 440 | Control lever, driven wheel side (first class lever) |
| 450 | Control lever, spring load side (first class lever) |
| 460 | Fulcrum of control lever |
| 465 | Member injection driven wheel axle |
| 470 | Straight cut hypoid gear |
| 480 | Bridge driving shaft |
| 490 | Pull-spring unloaded |
| 495 | Pull-spring loaded |
| 500 | Implantable part, member |

Helical guide drive 1", reference list:

| | |
|---|---|
| 710 | Distal inserter housing |
| 709 | Back wall for drive wheel |
| 711 | Sliding guide bars |
| 712 | Distal handhold |
| 713 | Access window |
| 714 | arm slot or keyway |
| 715 | needle guide port |
| 716 | bayonet slot |
| 717 | hole for pin |
| 718 | activation trigger aperture |
| 719 | disengage trigger aperture |
| 720 | Proximal actuator housing |
| 721 | Sliding guide |
| 722 | Proximal handhold |
| 723 | Assembly screw holes |
| 729 | Aperture for member 500, Needle orifice port |
| 730 | Needle part |
| 731 | Helical hollow needle, left-handed |
| 732 | Needle tip, distal hollow needle aperture |
| 733 | Proximal needle aperture |
| 734 | Needle stability tube |
| 735 | Helical hollow needle centrically bending section |
| 736 | Hollow needle tube section |
| 737 | Helical section affixed inside tube 734 |
| 738 | Sliding contact disc |
| 739 | Force distribution disc |
| 740 | Helical guide tube part |
| 741 | Tube |
| 742 | Docking cone |
| 743 | Arms |
| 744 | Helical guide tube |
| 745 | Distal guide orifice |
| 746 | Proximal guide orifice |
| 747 | Arm hole for pin |
| 750 | Trigger |
| 751 | Hole for thumb |
| 752 | Wings |
| 760 | bayonet mechanism |
| 761 | arm clearance slot |
| 762 | bayonet pins |
| 770 | fork pin mechanism Mechanism |

APPENDIX-continued

Element list

| | |
|---|---|
| 781 | Drive Wheel |
| 782 | Driven Wheel, |
| 783 | Axle pin for wheels |
| 784 | Activation Wheel, same diameter as 782 |
| 800 | Head and mandible fixation cage |

What is claimed is:

1. A helical inserter for inserting an insert helically into soft tissue including:
 a. a housing assembly;
 b. a hollow helical insert guide held in functional relationship by the housing assembly such that a proximal aperture of the insert guide is concentric with the housing assembly, wherein the insert guide is adapted to be loaded with the insert through the proximal aperture for helical transport therewith into the soft tissue;
 c. a helical insert guide drive which drives the helical insert guide in rotation into the soft tissue; and
 d. a guide removal device which, when an insert is present within the insert guide, removes the insert guide while leaving the insert in its intended implant location in the soft tissue.

2. The helical inserter of claim 1, wherein the helical insert guide drive comprises a cam surface which, when a cam follower mounted on a first housing component which moves relative thereto follows the cam surface, the guide drive drives the insert guide in rotation and translation.

3. The helical inserter of claim 2, wherein the cam surface of the helical insert guide drive is disposed in a helical groove cut in a first second housing component and the cam follower is affixed to the first housing component.

4. The helical inserter of claim 3, wherein, in the helical inserter guide drive, in order to drive the helical guide into the soft tissue, the first housing component is arranged to be rotated by the operator relative to the second housing component, the cam surface directing the cam follower so as to guide the insert guide in rotation and translation.

5. The helical inserter of claim 1, wherein the helical insert guide drive comprises a rack and pinion arrangement.

6. The helical inserter of the above claim 5, wherein the rack comprises an elongated surface and the pinion is a wheel which is frictionally engaged with the elongated surface.

7. The helical inserter of the above claim 6, wherein the pinion comprises a rubber surface.

8. The helical inserter of claim 1, wherein the helical insert guide drive converts defined relative translation between two assemblies into defined relative translational and rotational motion to the guide.

9. The helical inserter of claim 1, wherein a rack and pinion arrangement is used to drive a gear train which imparts defined relative translational and rotational motion to the guide.

10. The helical inserter of claim 1, wherein a helical guiding device imparts defined relative translational and rotational motion to the guide.

11. The helical inserter of the above claim 10, wherein the guiding device is a helical guiding device including a helical channel, the guiding device being held stationary with respect to a distal housing component of the housing assembly.

12. The helical inserter of claim 11, wherein the guiding device includes a drive train which maintains the position of the insert in the soft tissue as the drive train removes the insert guide.

13. The helical inserter of claim 11, wherein the guiding device includes at least one wing which engages into a corresponding slot so as to lock the guiding device against relative rotation with the distal housing component.

14. The helical inserter of claim 13, wherein a retaining device further retains the guiding device in nonrotating engagement with the distal housing component.

15. The helical inserter of claim 10, wherein the helical guiding device is removable so as to be interchangeable with other helical guiding devices of differing characteristics.

16. The helical inserter of claim 10, wherein the helical guiding device is affixed with a clip or retainer, such that it can be easily removed and another affixed.

17. The helical inserter of claim 10, wherein the guide removal device is driven by a rack and pinion arrangement.

18. The helical inserter of the above claim 17, wherein the rack comprises an elongated surface and the pinion is a wheel which frictionally engages the elongated surface.

19. The helical inserter of claim 10, wherein the guide removal device is driven, directly or indirectly, by the guiding device.

20. The helical inserter of the above claim 19, wherein the guiding device drives the guide to which a drive gear is attached which drives the guide removal device.

21. The helical inserter of claim 1, wherein the guide removal device is gear driven.

22. The helical inserter of the above claim 21, wherein the guide removal device includes an idler gear, selectively engageable by an operator in order to ensure select functioning for removal of the helical insert guide from the soft tissue.

23. A method of installing an insert helically into soft tissue, the method including the following steps;
 a. using a helical inserter of claim 1, load the hollow helical insert guide into the inserter;
 b. if the insert is not already loaded in the hollow insert guide, load the insert into the hollow helical insert guide;
 c. position the helical inserter against soft tissue, orienting the inserter along an axis along with insertion is desired;
 d. activating the helical inserter to insert the helical insert guide helically into soft tissue; and
 e. activating the guide removal device which, when the insert is present within the insert guide, removes the insert guide in helical rotation while leaving the insert in its intended implant location in the soft tissue.

24. The method of claim 23, wherein the soft tissue is of a living organism and wherein the method is adapted to insert an electrode or shape memory alloy helically into the living organism for treatment of sleep apnea.

25. A method of use of the helical inserter of claim 1 for the treatment of Sleep Apnea, the method including the following steps:
 a. place head of patient in fixed position using a rack;
 b. collect data of tongue in rest position and other deformation extremes, to create 3D model;
 c. determine needle size;
 d. place inserter in position or mount on the rack in order to ensure precise access through tissue in 3 dimensions;
 e. confirm desired position of tongue and head with a scan before inserting;

f. activate helical inserter mechanism to insert the insert helically in soft tissue; and g. optionally, confirm position with a scan.

26. The method of claim 25, wherein, in step (a), the data is gathered using a CT or MRI scan.

27. The method of claim 25, wherein in step (e), confirmation of position is performed using a CT scan or ultrasound.

28. A hollow helical insert guide for use with the helical inserter of claim 1, wherein the guide is a hollow needle having one end which is helically formed and another end which is substantially straight.

29. The hollow helical insert guide of claim 28, wherein an insert is pre-installed within the guide.

30. The hollow helical insert guide of claim 29, wherein the insert is selected from a group of inserts consisting of a regular electrode, a shape memory alloy and an electroactive polymer.

31. The hollow helical insert guide of claim 30, wherein a fluid is disposed between the insert and the guide.

32. The hollow helical insert guide of claim 31, wherein the fluid is an antiseptic fluid.

33. The hollow helical insert guide of claim 28, wherein the guide is disposable.

34. A helical inserter for inserting inserts helically into soft tissue, the inserter comprising:

(a) a housing assembly;

(b) a hollow helical needle;

(c) a first hypoid gear wheel concentrically affixed to the proximal side of the helical needle and held in axial position through the housing assembly for rotational insertion of the helical needle into the soft tissue; and (d) a second hypoid gear wheel matched to the first hypoid gear wheel and held in axial position through the housing assembly, the second gear wheel driving an implantable member insertion mechanism, the insertion mechanism adapted to insert an implantable member through the hollow helical needle into the soft tissue by means of the hollow helical needle which is rotationally and translationally driven into the soft tissue.

35. The helical inserter of claim 34, wherein the driving of the implantable member insertion mechanism is accomplished by a rack and pinion mechanism.

* * * * *